United States Patent [19]
Pastan et al.

[11] Patent Number: 6,147,203
[45] Date of Patent: Nov. 14, 2000

[54] RECOMBINANT DISULFIDE-STABILIZED POLYPEPTIDE FRAGMENTS HAVING BINDING SPECIFICITY

[75] Inventors: Ira H. Pastan; Byungkook Lee, both of Potomac; Sun-Hee Jung, Bethesda; Ulrich Brinkmann, Kensington, all of Md.

[73] Assignee: The United States of America as represented by the Department of Health and Human Services, Washington, D.C.

[21] Appl. No.: 09/002,753

[22] Filed: Jan. 5, 1998

Related U.S. Application Data

[62] Division of application No. 08/077,252, Jun. 14, 1993, Pat. No. 5,747,654.

[51] Int. Cl.[7] ............................. C07H 21/02; C07H 21/04
[52] U.S. Cl. ........................................ 536/23.53; 536/23.1
[58] Field of Search ................................. 536/23.1, 23.53

[56] References Cited

U.S. PATENT DOCUMENTS

| | | |
|---|---|---|
| 4,946,778 | 8/1990 | Ladner et al. . |
| 5,091,513 | 2/1992 | Huston et al. . |
| 5,132,405 | 7/1992 | Huston et al. . |

FOREIGN PATENT DOCUMENTS

| | | |
|---|---|---|
| 0 338 745 | 10/1989 | European Pat. Off. . |
| WO 93/06217 | 4/1993 | WIPO . |
| WOA93 07286 | 4/1993 | WIPO . |

OTHER PUBLICATIONS

R. Kreitman et al.: "The activity of disulfide–stabilized recombinant immunotoxin RFB4(dsFv)–PE38 towards human CD22+ lymphoma/leukemia xenografts in mice and fresh cells from patients." Proceedings of the American Association for Cancer Research, vol. 38, Mar. 1997, p. 28 XP002075139 USA see abstract #187.

J. De Kruif et al.: "Biosynthetically lipid–modified human scFv fragments from phage display libraries as targeting molecules for immunoliposomes." FEBS Letters, vol. 399,, No. 3, Dec. 16, 1996, pp. 232–236, XP002075140 Amsterdam, NL.

Y. Reiter et al.: "Stabilization of the Fv fragments in recombinant immunotoxins by disulfide bonds engineered into conserved framework regions." Biochemistry vol. 33, No. 18, May 10, 1994, pp. 5451–5459, XP002075141 Washington, D.C, USA.

R. Kreitman et al.: "Pseudomonas exotoxin–based imunotoxins containing the antibody LL2 or LL2–Fab' induce regression of subcutaneous human B–cell lymphoma in mice." Cancer Research, vol. 53, No. 4, Feb. 15, 1993, pp. 819–825, XP002075142 Baltimore, MD, USA.

C–T. Kuan et al. "Recombinant immunotoxin containing a disulfide–stabilized Fv directed at erbB2 that does not require proteolytic activation." Biochemistry, vol. 35, No. 9, Mar. 5, 1996, pp. 2872–2877, XP002075143 Washington, DC, USA.

V. Rajagopal et al.: "A form of anti–Tac(Fv) which is both single–chain and disulfide–stabilized for imaging CD25+ tumors." Proceedings of the American Association for Cancer Research, vol. 8, Mar. 1997, p. 27 XP002075144 USA see abstract #180.

D. Luo et al.: "V1–linker–Vh orientation–dependent expression of single chain Fv containing an engineered disulfide–stabilized bond in the framework regions." Journal of Biochemistry, vol. 118, No. 4, Oct. 1, 1995, pp. 825–831, XP002075145 Tokyo, Japan.

M. Rordigues et al.: "Development of a humanized disulfide–stabilized anti–p185HER2 Fv–betalactamase fusion protein for activation of a cephalosporin doxorubicin prodrug." Cancer Research, vol. 55, No. 1, Jan. 1, 1995, pp. 63–70, XP002075146 Baltimore, MD, USA.

E. Mansfield et al.: "Characterization of RFB4–Pseudomonas exotoxin A immunotoxins targeted to CD22 on B–cell malignancies." Bioconjugate Chemistry, vol. 7, No. 5, Sep. 1996, pp. 557–563, XP002075147 Washington, DC, USA.

E. Mansfield et al.: "Recombinant RFB4 immunotoxins exhibit potent cytotoxic activity for CD22–bearing cells and tumors." Blood, vol. 90, No. 5, Sep. 1, 1997, pp. 2020–2026, XP002075148 New York, NY, USA.

Batra et al., Proc. Natl. Acad. Sci. USA, 89:5967–5871 (1992).
Bird et al., Science, 242:423–426 (1988).
Brinkmann et al., J. Immunology, 150:2774–2782 (1993).
Brinkmann et al., Proc. Natl. Acad. Sci., 90:7538–7542 (Aug. 1993).
Brinkmann et al., Proc. Natl. Acad. Sci., 88:8616–8620 (Oct. 1991).
Buchner et al., Anal. Biochem., 205:263–270 (1992).
Cumber et al., J. Immunology, 149(1) :120–126 (Jul. 1, 1992).
Dillman, Ann. Internal. Med., 111:592–600 (1989).
Glockshuber et al., Biochemistry, 29:1362–1367 (1990).
Glockshuber et al., Biochemistry, 31(5) :1270–1279 (Feb. 11, 1992).

(List continued on next page.)

Primary Examiner—Christina Y. Chan
Assistant Examiner—Gerald R. Ewoldt
Attorney, Agent, or Firm—Townsend and Townsend and Crew LLP

[57] ABSTRACT

The present invention relates to disulfide-stabilized recombinant polypeptide molecules which have the binding ability and specificity for another peptide, such as the variable region of an antibody molecule. Methods of producing these molecules and nucleic acid sequences encoding these molecules are also described. In particular, the invention discloses Fv antibody fragments stabilized by a disulfide bond connecting the $V_H$ and $V_L$ regions of the Fv fragment. The α and β chains of T cell receptors may be similarly stabilized by means described in the invention.

8 Claims, 5 Drawing Sheets

OTHER PUBLICATIONS

Harris et al. *TIBTECH*, 11:42–42 (1993).

Huston et al., *Proc. Natl. Acad. Sci. USA*, 85:5879–5883 (1988).

Hird et al., *Genes and Cancer* (1990) chapter 17 pp. 183–189.

Kasprzyk et al., *Cancer Research*, 53:2771–2776 (May 15, 1992).

Kuruez et al., *Proc. Natl. Acad. Sci.*, 90:3830–3834 (May 1993).

Osband et al., *Immunotherapy*, 11(6):193–195 (1990).

Pantoliano et al., *Biochemistry*, 30:10117–10125 (1991).

Reiter et al., *Biochemistry* 33:5451–5459 (May 10, 1994).

Reiter et al., *J. Biological Chemistry*, 269(28):18327–1833 (Jul. 15, 1994).

Stemmer et al., *Biotechniques*, 14(2):256–265 (1993).

Pack et al., *Biochemistry*, 31:1579–1584 (1992).

Waldmann, *Science*, 252:1657–1662 (1991).-

```
                          FR1                        CDR1                              FR2
603(VL)  DIVMTQSPSSLSVSAGERVTMSC  KSSQSLLNSGNQKNFLA  WYQQKPGQPPKLLIY
         |::||||||||:|||:|||||:     |:||  ::||||||    ||:||||:|||||
B3(VL)   DVLMTQSPLSLPVSLGDQASISC  RSSQIIVHS.NGNTYLE  WYLQKPGQSPKLLIY

FR4
         *                                                      CDR3       |
603(VL)  GASTRES  GVPDRFTGSGSGTDFTLTISSVQAEDLAVYYC  QNDHSYPLT  FGAGTK
         |  |||   ||||||:||||||||||||:|||||:|:|||   ::|| ||    |||
B3(VL)   KVSNRFS  GVPDRFSGSGSGTDFTLKISRVEAEDLGVYYC  FQGSHVPFT  FGSG
                                    FR3                                    △

FR1                         CDR1                              FR2
603(VH)  EVKLVESGGGLVQPGGSLRLSCATSGFTFS  DFYME  WVRQPPGKRLEWIA  ASRNKG
         ||||||||||||||||||||:|||||||||   |::|  |||||||||||||    |
B3(VH)   DVKLVESGGGLVQPGGSLKLSCATSGFTFS  DYYMY  WVRQTPEKRLEWVA  YISN..

*          CDR2
603(VH)  NKYTTEYSASVKG  RFIVSRDTSQSILYLQMNALRAEDTAIYYCAR  NYYGSTWYFDV
         :  :|||| ||||  ||||||:|||||||||:|||||||:||||||   |
B3(VH)   DDSSAAYSDTVKG  RFTISRDNARNTLYLQMSRLKSEDTAIYYCAR  G.LAWGAWFAY
                                      FR3                                      △        CDR3

603(VH)  WGAGTTVTVS
         ||| || |||
B3(VH)   WGQGTLVTVS
              FR4
```

FIG. 1.

VHR44C/VLS105C

VH FR2

| | | | | | | | | | | | | |
|---|---|---|---|---|---|---|---|---|---|---|---|---|
| 603 | W | V | R | Q | P | P | G | K | R | L | E | W | I | A |
| B3 | W | V | R | Q | T | P | E | K | [R] | L | E | W | V | A |
| e23 | W | V | K | Q | S | H | G | K | [N] | L | E | W | I | G |
| aTac | W | V | K | Q | R | P | G | Q | [G] | L | E | W | I | G |

VL FR4

| | | | | | | |
|---|---|---|---|---|---|---|
| 603 | F | G | A | G | T | K |
| B3 | F | G | [S] | G | | |
| e23 | F | G | [G] | G | S | K |
| aTac | F | G | [S] | G | T | K |

FIG. 4.

SEQUENCE LISTING (1) GENERAL INFORMATION:

(iii) NUMBER OF SEQUENCES: 23

(2) INFORMATION FOR SEQ ID NO:1:

(i) SEQUENCE CHARACTERISTICS:
      (A) LENGTH: 118 amino acids
      (B) TYPE: amino acid
      (C) STRANDEDNESS:
      (D) TOPOLOGY: linear (ii) MOLECULE TYPE: protein (ix) FEATURE:
      (A) NAME/KEY: Protein
      (B) LOCATION: 1..118
      (D) OTHER INFORMATION: /note= "Monoclonal antibody B3 Heavy
         chain variable region (V-H)"

(ix) FEATURE:
      (A) NAME/KEY: Region
      (B) LOCATION: 1..30
      (D) OTHER INFORMATION: /label= FR1
         /note= "Framework Region 1 (FR1)"

(ix) FEATURE:
      (A) NAME/KEY: Region
      (B) LOCATION: 31..35
      (D) OTHER INFORMATION: /label= CDR1
         /note= "Complementarity Determining
         Region 1 (CDR1)"

(ix) FEATURE:
      (A) NAME/KEY: Region
      (B) LOCATION: 36..49
      (D) OTHER INFORMATION: /label= FR2
         /note= "Framework Region 2 (FR2)"

(ix) FEATURE:
      (A) NAME/KEY: Region
      (B) LOCATION: 50..66

```
            (D) OTHER INFORMATION: /label= CDR2
                /note= "Complementarity Determining
                Region 2 (CDR2)"

(ix) FEATURE:
            (A) NAME/KEY: Region
            (B) LOCATION: 67..98
            (D) OTHER INFORMATION: /label= FR3
                /note= "Framework Region 3 (FR3)"

(ix) FEATURE:
            (A) NAME/KEY: Region
            (B) LOCATION: 99..108
            (D) OTHER INFORMATION: /label= CDR3
                /note= "Complementarity Determining
                Region 3 (CDR3)"

(ix) FEATURE:
            (A) NAME/KEY: Region
            (B) LOCATION: 109..118
            (D) OTHER INFORMATION: /label= FR4
                /note= "Framework Region 4 (FR4)"

(xi) SEQUENCE DESCRIPTION: SEQ ID NO:1:

Asp Val Lys Leu Val Glu Ser Gly Gly Gly Leu Val Gln Pro Gly Gly
1               5                  10                  15

Ser Leu Lys Leu Ser Cys Ala Thr Ser Gly Phe Thr Phe Ser Asp Tyr
            20                  25                  30

Tyr Met Tyr Trp Val Arg Gln Thr Pro Glu Lys Arg Leu Glu Trp Val
        35                  40                  45

Ala Tyr Ile Ser Asn Asp Ser Ser Ala Ala Tyr Ser Asp Thr Val
    50                  55                  60

Lys Gly Arg Phe Thr Ile Ser Arg Asp Asn Ala Arg Asn Thr Leu Tyr
65                  70                  75                  80

Leu Gln Met Ser Arg Leu Lys Ser Glu Asp Thr Ala Ile Tyr Tyr Cys
                85                  90                  95

Ala Arg Gly Leu Ala Trp Gly Ala Trp Phe Ala Tyr Trp Gly Gln Gly
                100                 105                 110

Thr Leu Val Thr Val Ser
        115

(2) INFORMATION FOR SEQ ID NO:2:

(i) SEQUENCE CHARACTERISTICS:
            (A) LENGTH: 121 amino acids
            (B) TYPE: amino acid
            (C) STRANDEDNESS:
            (D) TOPOLOGY: linear (ii) MOLECULE TYPE: protein (ix) FEATURE:
            (A) NAME/KEY: Protein
            (B) LOCATION: 1..121
            (D) OTHER INFORMATION: /note= "Monoclonal antibody McPC603
                Heavy chain variable region (V-H)"

(ix) FEATURE:
            (A) NAME/KEY: Region
            (B) LOCATION: 1..30
            (D) OTHER INFORMATION: /label= FR1
                /note= "Framework Region 1 (FR1)"

(ix) FEATURE:
            (A) NAME/KEY: Region
            (B) LOCATION: 31..35
            (D) OTHER INFORMATION: /label= CDR1
                /note= "Complementarity Determining
                Region 1 (CDR1)"
```

```
    (ix) FEATURE:
          (A) NAME/KEY: Region
          (B) LOCATION: 36..49
          (D) OTHER INFORMATION: /label= FR2
              /note= "Framework Region 2 (FR2)"

(ix) FEATURE:
          (A) NAME/KEY: Region
          (B) LOCATION: 50..68
          (D) OTHER INFORMATION: /label= CDR2
              /note= "Complementarity Determining
              Region 2 (CDR2)"

(ix) FEATURE:
          (A) NAME/KEY: Region
          (B) LOCATION: 69..100
          (D) OTHER INFORMATION: /label= FR3
              /note= "Framework Region 3 (FR3)"

(ix) FEATURE:
          (A) NAME/KEY: Region
          (B) LOCATION: 101..111
          (D) OTHER INFORMATION: /label= CDR3
              /note= "Complementarity Determining
              Region 3 (CDR3)"

(ix) FEATURE:
          (A) NAME/KEY: Region
          (B) LOCATION: 112..121
          (D) OTHER INFORMATION: /label= FR4
              /note= "Framework Region 4 (FR4)"

(xi) SEQUENCE DESCRIPTION: SEQ ID NO:2:

Glu Val Lys Leu Val Glu Ser Gly Gly Gly Leu Val Gln Pro Gly Gly
1               5                  10                  15

Ser Leu Arg Leu Ser Cys Ala Thr Ser Gly Phe Thr Phe Ser Asp Phe
            20                  25                  30

Tyr Met Glu Trp Val Arg Gln Pro Pro Gly Lys Arg Leu Glu Trp Ile
        35                  40                  45

Ala Ala Ser Arg Asn Lys Gly Asn Lys Tyr Thr Thr Glu Tyr Ser Ala
    50                  55                  60

Ser Val Lys Gly Arg Phe Ile Val Ser Arg Asp Thr Ser Gln Ser Ile
65                  70                  75                  80

Leu Tyr Leu Gln Met Asn Ala Leu Arg Ala Glu Asp Thr Ala Ile Tyr
                85                  90                  95

Tyr Cys Ala Arg Asn Tyr Tyr Gly Ser Thr Trp Tyr Phe Asp Val Trp
            100                 105                 110

Gly Ala Gly Thr Thr Val Thr Val Ser
            115                 120

(2) INFORMATION FOR SEQ ID NO:3:

(i) SEQUENCE CHARACTERISTICS:
          (A) LENGTH: 112 amino acids
          (B) TYPE: amino acid
          (C) STRANDEDNESS:
          (D) TOPOLOGY: linear (ii) MOLECULE TYPE: protein (ix) FEATURE:
          (A) NAME/KEY: Protein
          (B) LOCATION: 1..112
          (D) OTHER INFORMATION: /note= "Monoclonal antibody B3 Light
              chain variable region (V-L)"

(ix) FEATURE:
          (A) NAME/KEY: Region
          (B) LOCATION: 1..23
          (D) OTHER INFORMATION: /label= FR1
```

```
            /note= "Framework Region 1 (FR1)"

(ix) FEATURE:
    (A) NAME/KEY: Region
    (B) LOCATION: 24..39
    (D) OTHER INFORMATION: /label= CDR1
        /note= "Complementarity Determining
        Region 1 (CDR1)"

(ix) FEATURE:
    (A) NAME/KEY: Region
    (B) LOCATION: 40..54
    (D) OTHER INFORMATION: /label= FR2
        /note= "Framework Region 2 (FR2)"

(ix) FEATURE:
    (A) NAME/KEY: Region
    (B) LOCATION: 55..61
    (D) OTHER INFORMATION: /label= CDR2
        /note= "Complementarity Determining
        Region 2 (CDR2)"

(ix) FEATURE:
    (A) NAME/KEY: Region
    (B) LOCATION: 62..93
    (D) OTHER INFORMATION: /label= FR3
        /note= "Framework Region 3 (FR3)"

(ix) FEATURE:
    (A) NAME/KEY: Region
    (B) LOCATION: 94..102
    (D) OTHER INFORMATION: /label= CDR3
        /note= "Complementarity Determining
        Region 3 (CDR3)"

(ix) FEATURE:
    (A) NAME/KEY: Region
    (B) LOCATION: 103..106
    (D) OTHER INFORMATION: /label= FR4
        /note= "Framework Region 4 (FR4)"

(xi) SEQUENCE DESCRIPTION: SEQ ID NO:3:

Asp Val Leu Met Thr Gln Ser Pro Leu Ser Leu Pro Val Ser Leu Gly
1               5                   10                  15

Asp Gln Ala Ser Ile Ser Cys Arg Ser Ser Gln Ile Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
            85                  90                  95

Ser His Val Pro Phe Thr Phe Gly Ser Gly Thr Lys Leu Glu Ile Lys
                100                 105                 110

(2) INFORMATION FOR SEQ ID NO:4:

(i) SEQUENCE CHARACTERISTICS:
        (A) LENGTH: 113 amino acids
        (B) TYPE: amino acid
        (C) STRANDEDNESS:
        (D) TOPOLOGY: linear (ii) MOLECULE TYPE: protein (ix) FEATURE:
        (A) NAME/KEY: Protein
        (B) LOCATION: 1..113
        (D) OTHER INFORMATION: /note= "Monoclonal antibody McPC603
```

Light chain variable region (V-L)"

(ix) FEATURE:
    (A) NAME/KEY: Region
    (B) LOCATION: 1..23
    (D) OTHER INFORMATION: /label= FR1
        /note= "Framework Region 1 (FR1)"

(ix) FEATURE:
    (A) NAME/KEY: Region
    (B) LOCATION: 24..40
    (D) OTHER INFORMATION: /label= CDR1
        /note= "Complementarity Determining
        Region 1 (CDR1)"

(ix) FEATURE:
    (A) NAME/KEY: Region
    (B) LOCATION: 41..55
    (D) OTHER INFORMATION: /label= FR2
        /note= "Framework Region 2 (FR2)"

(ix) FEATURE:
    (A) NAME/KEY: Region
    (B) LOCATION: 56..62
    (D) OTHER INFORMATION: /label= CDR2
        /note= "Complementarity Determining
        Region 2 (CDR2)"

(ix) FEATURE:
    (A) NAME/KEY: Region
    (B) LOCATION: 63..94
    (D) OTHER INFORMATION: /label= FR3
        /note= "Framework Region 3 (FR3)"

(ix) FEATURE:
    (A) NAME/KEY: Region
    (B) LOCATION: 95..103
    (D) OTHER INFORMATION: /label= CDR3
        /note= "Complementarity Determining
        Region 3 (CDR3)"

(ix) FEATURE:
    (A) NAME/KEY: Region
    (B) LOCATION: 104..109
    (D) OTHER INFORMATION: /label= FR4
        /note= "Framework Region 4 (FR4)"

(xi) SEQUENCE DESCRIPTION: SEQ ID NO:4:

Asp Ile Val Met Thr Gln Ser Pro Ser Ser Leu Ser Val Ser Ala Gly
1               5                   10                  15

Glu Arg Val Thr Met Ser Cys Lys Ser Ser Gln Ser Leu Leu Asn Ser
            20                  25                  30

Gly Asn Gln Lys Asn Phe Leu Ala Trp Tyr Gln Lys Pro Gly Gln
        35                  40                  45

Pro Pro Lys Leu Leu Ile Tyr Gly Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp His Ser Tyr Pro Leu Thr Phe Gly Ala Gly Thr Lys Leu Glu Ile
                100                 105                 110

Lys (2) INFORMATION FOR SEQ ID NO:5:

(i) SEQUENCE CHARACTERISTICS:
        (A) LENGTH: 34 base pairs
        (B) TYPE: nucleic acid
        (C) STRANDEDNESS: single (D) TOPOLOGY: linear (ii) MOLECULE TYPE: DNA (xi) SEQUENCE DESCRIPTION: SEQ ID NO:5:

TATGCGACCC ACTCGAGACA CTTCTCTGGA GTCT                                      34

(2) INFORMATION FOR SEQ ID NO:6:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:6:

TTTCCAGCTT TGTCCCACAG CCGAACGTGA ATGG                                      34

(2) INFORMATION FOR SEQ ID NO:7:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:7:

CCGCCACCAC CGGATCCGCG AATTCATTAG GAGACAGTGA CCAGAGTC                       48

(2) INFORMATION FOR SEQ ID NO:8:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:8:

TCGGTTGGAA ACTTTGCAGA TCAGGAGCTT TGGAGAC                                   37

(2) INFORMATION FOR SEQ ID NO:9:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:9:

TCGGTTGGAA ACGCAGTAGA TCAGAAGCTT TGGAGAC                                   37

(2) INFORMATION FOR SEQ ID NO:10:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:10:

AGTAAGCAAA CCAGGCGCAC CAGGCCAGTC CTCTTGCGCA GTAATATATG GC        52

(2) INFORMATION FOR SEQ ID NO:11:

(i) SEQUENCE CHARACTERISTICS:
            (A) LENGTH: 52 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:11:

AGTAAGCAAA ACAGGCTCCC CAGGCCAGTC CTCTTGCGCA GTAATATATG GC        52

(2) INFORMATION FOR SEQ ID NO:12:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:12:

AGTCCAATCC ACTCGAGGCA CTTTCCATGG CTCTGC        36

(2) INFORMATION FOR SEQ ID NO:13:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:13:

TATTTCCAGC TTGGACCCAC ATCCGAACGT GGGTGG        36

(2) INFORMATION FOR SEQ ID NO:14:

(i) SEQUENCE CHARACTERISTICS:
            (A) LENGTH: 50 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:14:

AGAAGATTTA CCAGAACCAG GAATTCATTA TTTTATTTCC AGCTTGGACC        50

(2) INFORMATION FOR SEQ ID NO:15:

(i) SEQUENCE CHARACTERISTICS:
            (A) LENGTH: 14 amino acids
            (B) TYPE: amino acid
            (C) STRANDEDNESS:
            (D) TOPOLOGY: linear (ii) MOLECULE TYPE: peptide (ix) FEATURE:
            (A) NAME/KEY: Peptide
            (B) LOCATION: 1..14
            (D) OTHER INFORMATION: /label= FR2

/note= "Framework Region 2 (FR2) from
            Monoclonal antibody McPC603 Heavy chain
            variable region (V-H)"

(xi) SEQUENCE DESCRIPTION: SEQ ID NO:15:

Trp Val Arg Gln Pro Pro Gly Lys Arg Leu Glu Trp Ile Ala
1               5                   10

(2) INFORMATION FOR SEQ ID NO:16:

(i) SEQUENCE CHARACTERISTICS:
        (A) LENGTH: 14 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Peptide
        (B) LOCATION: 1..14
        (D) OTHER INFORMATION: /label= FR2
            /note= "Framework Region 2 (FR2) from
            Monoclonal antibody B3 Heavy chain
            variable region (V-H)"

(xi) SEQUENCE DESCRIPTION: SEQ ID NO:16:

Trp Val Arg Gln Thr Pro Glu Lys Arg Leu Glu Trp Val Ala
1               5                   10

(2) INFORMATION FOR SEQ ID NO:17:

(i) SEQUENCE CHARACTERISTICS:
        (A) LENGTH: 14 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Peptide
        (B) LOCATION: 1..14
        (D) OTHER INFORMATION: /label= FR2
            /note= "Framework Region 2 (FR2) from
            Monoclonal antibody e23 Heavy chain
            variable region (V-H)"

(xi) SEQUENCE DESCRIPTION: SEQ ID NO:17:

Trp Val Lys Gln Ser His Gly Lys Asn Leu Glu Trp Ile Gly
1               5                   10

(2) INFORMATION FOR SEQ ID NO:18:

(i) SEQUENCE CHARACTERISTICS:
        (A) LENGTH: 14 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Peptide
        (B) LOCATION: 1..14
        (D) OTHER INFORMATION: /label= FR2
            /note= "Framework Region 2 (FR2) from
            Monoclonal antibody aTac Heavy chain
            variable region (V-H)"

(xi) SEQUENCE DESCRIPTION: SEQ ID NO:18:

Trp Val Lys Gln Arg Pro Gly Gln Gly Leu Glu Trp Ile Gly

```
1               5              10
```

(2) INFORMATION FOR SEQ ID NO:19:

(i) SEQUENCE CHARACTERISTICS:
        (A) LENGTH: 6 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Peptide
        (B) LOCATION: 1..6
        (D) OTHER INFORMATION: /label= FR4
            /note= "Framework Region 4 (FR4) from
            Monoclonal antibody McPC603 Light chain
            variable region (V-L)"

(xi) SEQUENCE DESCRIPTION: SEQ ID NO:19:

```
Phe Gly Ala Gly Thr Lys
1               5
```

(2) INFORMATION FOR SEQ ID NO:20:

(i) SEQUENCE CHARACTERISTICS:
        (A) LENGTH: 4 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Peptide
        (B) LOCATION: 1..4
        (D) OTHER INFORMATION: /label= FR4
            /note= "Framework Region 4 (FR4) from
            Monoclonal antibody B3 Light chain
            variable region (V-L)"

(xi) SEQUENCE DESCRIPTION: SEQ ID NO:20:

```
Phe Gly Ser Gly
1
```

(2) INFORMATION FOR SEQ ID NO:21:

(i) SEQUENCE CHARACTERISTICS:
        (A) LENGTH: 6 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Peptide
        (B) LOCATION: 1..6
        (D) OTHER INFORMATION: /label= FR4
            /note= "Framework Region 4 (FR4) from
            Monoclonal antibody e23 Light chain
            variable region (V-L)"

(xi) SEQUENCE DESCRIPTION: SEQ ID NO:21:

```
Phe Gly Gly Gly Ser Lys
1               5
```

(2) INFORMATION FOR SEQ ID NO:22:

(i) SEQUENCE CHARACTERISTICS:
        (A) LENGTH: 6 amino acids

-continued

```
            (B) TYPE: amino acid
            (C) STRANDEDNESS:
            (D) TOPOLOGY: linear (ii) MOLECULE TYPE: peptide (ix) FEATURE:
            (A) NAME/KEY: Peptide
            (B) LOCATION: 1..6
            (D) OTHER INFORMATION: /label= FR4
                  /note= "Framework Region 4 (FR4) from
                  Monoclonal antibody aTac Light chain
                  variable region (V-L)"

(xi) SEQUENCE DESCRIPTION: SEQ ID NO:22:

Phe Gly Ser Gly Thr Lys
1               5

(2) INFORMATION FOR SEQ ID NO:23:

(i) SEQUENCE CHARACTERISTICS:
            (A) LENGTH: 15 amino acids
            (B) TYPE: amino acid
            (C) STRANDEDNESS:
            (D) TOPOLOGY: linear (ii) MOLECULE TYPE: peptide (ix) FEATURE:
            (A) NAME/KEY: Peptide
            (B) LOCATION: 1..15
            (D) OTHER INFORMATION: /note= "(Gly-4Ser)-3 peptide linker"

(xi) SEQUENCE DESCRIPTION: SEQ ID NO:23:

Gly Gly Gly Gly Ser Gly Gly Gly Gly Ser Gly Gly Gly Gly Ser
1               5                  10                  15
```

RECOMBINANT DISULFIDE-STABILIZED POLYPEPTIDE FRAGMENTS HAVING BINDING SPECIFICITY

This application is a divisional of and claims the benefit of U.S. application Ser. No. 08/077,252, filed Jun. 14, 1993, now U.S. Pat. No. 5,747,654 the disclosure of which is incorporated by reference.

BACKGROUND OF THE INVENTION

1. Field of the Invention

The present invention relates to disulfide-stabilized (ds) recombinant polypeptide molecules, such as the variable region of an antibody molecule, which have the binding ability and specificity for another peptide. Methods of producing these molecules and nucleic acid sequences encoding these molecules are also described.

2. In the Background

Antibodies are molecules that recognize and bind to a specific cognate antigen. Numerous applications of hybridoma-produced monoclonal antibodies for use in clinical diagnosis, treatment, and basis scientific research have been described. Clinical treatments of cancer, viral and microbial infections, B cell immunodeficiencies, and other diseases and disorders of the immune system using monoclonal antibodies appear promising. Fv fragments of immunoglobulins are considered the smallest functional component of antibodies required for high affinity binding of antigen. Their small size makes them potentially more useful than whole antibodies for clinical applications like imaging tumors and directing recombinant immunotoxins to tumors since size strongly influences tumor and tissue penetration.

Fv fragments are heterodimers of the variable heavy chain domain ($V_H$) and the variable light chain domain ($V_L$). The heterodimers of heavy and light chain domains that occur in whole IgG, for example, are connected by a disulfide bond. The Fv fragments are not and therefore Fvs alone are unstable. Glockshuber et al., *Biochemistry* 29:1362–1367 (1990). Recombinant Fvs which have $V_H$ and $V_L$ are connected by a peptide linker are typically stable, see, for example, Huston et al., *Proc. Natl. Acad, Sci. USA* 85:5879–5883 (1988) and Bird et al., *Science* 242:423–426 (1988). These are single chain Fvs which have been found to retain specificity and affinity and have been shown to be useful for imaging tumors and to make recombinant immunotoxins, for tumor therapy for example. However, researchers have bound that some of the single chain Fvs have a reduced affinity for antigen and the peptide linker can interfere with binding.

Another approach to stabilize the Fvs was attempted by Glockshuber et al., supra. Disulfide bonds were placed in the complementarity determining regions (CDR) of an antibody whose structure was known in a manner that had limited or no effect on ligand binding. This approach is problematic for stabilizing other Fvs with unknown structures because the structure of each CDR region changes from one antibody to the next and because disulfide bonds that bridge CDRs will likely interfere with antigen binding. Thus, it would be desirable to have alternative means to stabilize the Fv portions of an antibody of interest which would allow the affinity for the target antigen to be maintained.

SUMMARY OF THE INVENTION

The invention relates to a polypeptide specifically binding a ligand, wherein the polypeptide comprises a first variable region of a ligand binding moiety bound through a disulfide bond to a second separate variable region of the ligand binding moiety, the bond connecting framework regions of the first and second variable regions. The polypeptide may be conjugated to a radioisotope, an enzyme, a toxin, or a drug or may be recombinantly fused to a toxin, enzyme or a drug, for example. Nucleic acid sequences coding the polypeptides and pharmaceutical compositions containing them are also disclosed.

The polypeptide is preferably one, wherein the first variable region is a light chain variable region of an antibody and the second variable region is a heavy chain variable region of the antibody. The polypeptide may also be one, wherein the first variable region is an α variable chain region of a T cell receptor and the second variable region is a β variable chain region of the T cell receptor.

Methods for producing a disulfide stabilized polypeptide of a ligand binding moiety having a two variable regions are also disclosed comprising the following steps:

(a) mutating a nucleic acid for the first variable region so that cysteine is encoded at position 42, 43, 44, 45 or 46, and mutating a nucleic acid sequence for the second variable region so that cysteine is encoded at position 103, 104, 105, or 106, such positions being determined in accordance with the numbering scheme published by Kabat and Wu, corresponding to a light chain and a heavy chain region, respectively, of an antibody; or (b) mutating a nucleic acid for the first variable region so that cysteine is encoded at position 43, 44, 45, 46 or 47 and mutating a nucleic acid for the second variable region so that cysteine is encoded at position 98, 99, 100, or 101 such positions being determined in accordance with the numbering scheme published by Kabat and Wu, corresponding to a heavy chain or a light chain region respectively or an antibody; then (c) expressing the nucleic acid for the first variable region and the nucleic acid for the second variable region in an expression system; and (d) recovering the polypeptide having a binding affinity for the antigen.

The invention provides an alternative means to recombinant Fvs which have $V_H$ and $V_L$ connected by a peptide linker. Though such recombinant single chain Fvs are typically stable and specific, some have a reduced affinity for antigen and the peptide linker can interfere with binding. A means to produce recombinant Fv polypeptides that are stabilized by a disulfide bond located in the conserved regions of the Fv fragment and compositions that include these, such as immunotoxins, are also described.

The clinical administration of the small polypeptides of the invention affords a number of advantages over the use of larger fragments or entire antibody molecules. The polypeptides of this invention in preferred forms have greater stability due to the additional disulfide bond. Due to their small size they also offer fewer cleavage sites to circulating proteolytic enzymes resulting in greater stability. They reach their target tissue more rapidly, and are cleared more quickly from the body. They also have reduced immunogenicity. In addition, their small size facilitates specific coupling to other molecules in drug targeting and imaging applications.

The invention also provides a means of stabilizing the antigen-binding portion (the V domain) of the T cell receptors, by connecting the α and β chains of the V domain by an inter-chain disulfide bond. Such stabilization of the V domain will help isolate and purify this fragment in soluble form. The molecule can then be used in applications similar to those of other Fvs. They can be used in diagnostic assays for tumor cells or for detection of immune-based diseases such as autoimmune diseases and AIDS. They may also have therapeutic use as a target for tumor cells or as a means to block undesirable immune responses in autoimmune diseases, or other immune-based disease.

BRIEF DESCRIPTION OF THE FIGURES

FIG. 1: Sequence comparison of the heavy and light chain variable regions of MAb B3 (second row) and MAb McPC603 (first row). The solid line and the dot(s) between two sequences indicate identity and similarity, respectively. A space was inserted between the framework (FR) and the complementarity determining (CDR) regions, which are indicated above the first row and below subsequent rows of the respective sequences. The residues that can be changed to Cys for the preferred S1 site interchain disulfide bond are marked by a triangle below the sequence. In the sequence listing, heavy chain of MAb B3 is SEQ ID NO:1, heavy chain of MAb McPC603 is SEQ ID NO:2, light chain of MAb B3 is SEQ ID NO:3, and light chain of MAb McPC603 is SEQ ID NO:4. The assignment of framework (FR1–4) and complementarity determining regions (CDR1–3) is according to Kabat et al., infra.

FIG. 4: Amino acid sequence comparison of the heavy and light chain framework regions (FR2 and FR4, respectively) of MAb (monoclonal antibody) McPC603 ("603"), MAb B3 ("B3"), MAb e23 ("e23") and MAb aTac ("aTac") (SEQ ID NOs:15–22).

DETAILED DESCRIPTION

Figure 2:
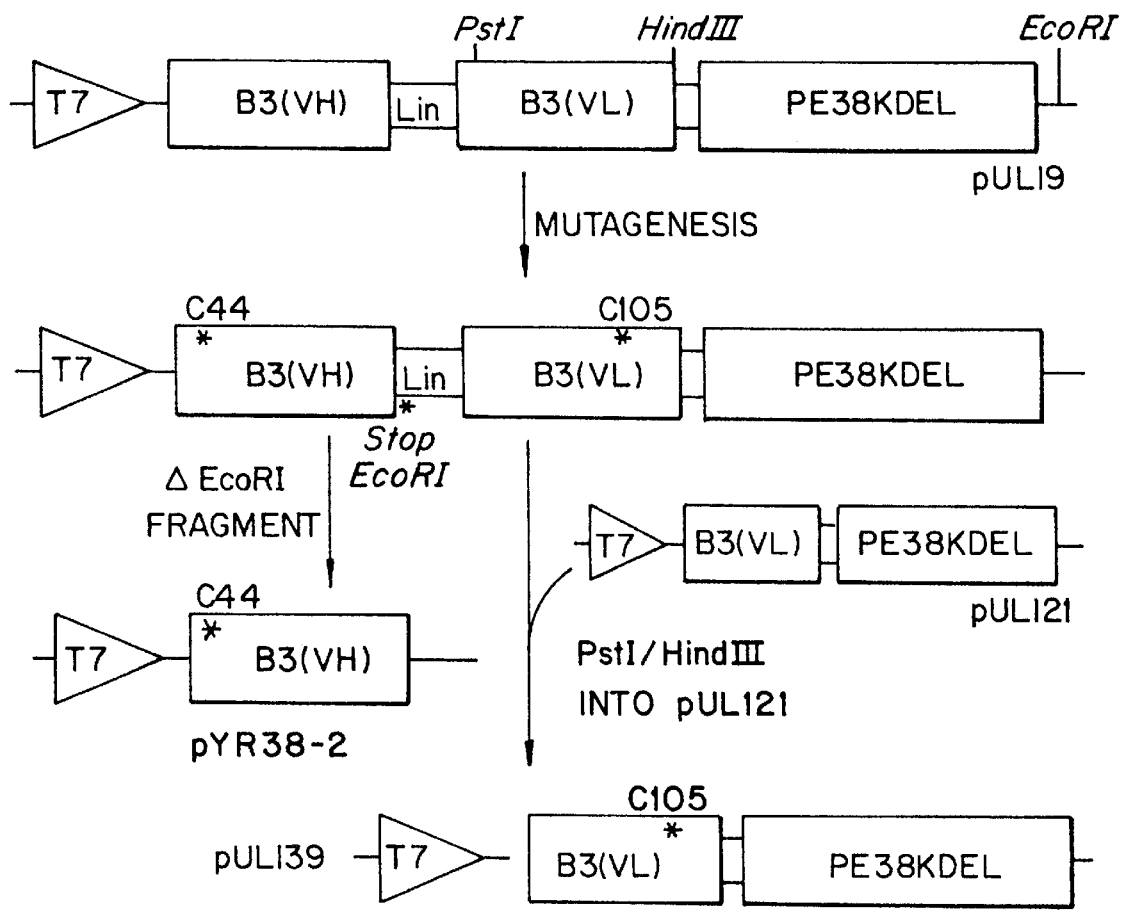
FIG. 2: Plasmids for expression of B3(dsFv)-immunotoxins. Single stranded uracil containing DNA of pULI28 was the template to mutate Arg44 of B3($V_H$) and Ser105 of B3($V_L$) to cys by Kunkel mutagenesis. The expression plasmid pYR38-2 for B3($V_H$Cys44) was generated by deletion of a $V_L$-PE38KDEL encoding EcoRI-fragment. pULI39 encoding B3($V_L$Cys105)-PE38KDEL was constructed by subcloning a $V_L$-Cys105 containing PstI-HindIII fragment into pULI21 that encodes B3($V_L$)-PE38KDEL.

This invention disclosed stable polypeptides which are capable of specifically binding ligands and which have two variable regions (such as light and heavy chain variable regions) bound together through a disulfide bond occurring in the framework regions of each variable region. These polypeptides are highly stable and have high binding affinity. They are produced by mutating nucleic acid sequences for each region so that cysteine is encoded at specific points in the framework regions of the polypeptide.

General Immunoglobulin Structure

Members of the immunoglobulin family all share an immunoglobulin-like domain characterized by a centrally placed disulfide bridge that stabilizes a series of antiparallel β strands into an immunoglobulin-like fold. Members of the family (e.g., MHC class I, class II molecules, antibodies and T cell receptors) can share homology with either immunoglobulin variable or constant domains. An antibody heavy or light chain has an N-terminal ($NH_2$) variable region (V), and a C-terminal (—COOH) constant region (C). The heavy chain variable region is referred to as $V_H$, and the light chain variable region is referred to as $V_L$. $V_H$ and $V_L$ fragments together are referred to as "Fv". The variable region is the part of the molecule that binds to the antibody's cognate antigen, while the constant region determines the antibody's effector function (e.g., complement fixation, opsonization). Full-length immunoglobulin or antibody "light chains" (generally about 25 kilodaltons (Kd), about 214 amino acids) are encoded by a variable region gene at the N-terminus (generally about 110 amino acids) and a constant region gene at the COOH-terminus. Full-length immunoglobulin or antibody "heavy chains" (generally about 50 Kd, about 446 amino acids), are similarly encoded by a variable region gene (generally encoding about 116 amino acids) and one of the constant region genes (encoding about 330 amino acids). Typically, the "$V_L$" will include the portion of the light chain encoded by the $V_L$ and $J_L$ (J or joining region) gene segments, and the "$V_H$" will include the portion of the heavy chain encoded by the $V_H$, and $D_H$ (D or diversity region) and $J_H$ gene segments. See generally, Roitt, et al., *Immunology,* Chapter 6, (2d ed. 1989) and Paul, *Fundamental Immunology;* Raven Press (2d ed. 1989), both incorporated by reference herein.

An immunoglobulin light or heavy chain variable region comprises three hypervariable regions, also called complementarity determining regions or CDRs, flanked by four relatively conserved framework regions or FRs. Numerous framework regions and CDRs have been described (see, "Sequences of Proteins of Immunological Interest," E. Kabat, et al., U.S. Government Printing Office, NIH Publication No. 91-3242 (1991); which is incorporated herein by reference ("Kabat and Wu")). The sequences of the framework regions of different light or heavy chains are relatively conserved. The CDR and FR polypeptide segments are designated empirically based on sequence analysis of the Fv region of preexisting antibodies or of the DNA encoding them. From alignment of antibody sequences of interest with those published in Kabat and Wu and elsewhere, framework regions and CDRs can be determined for the antibody or other ligand binding moiety of interest. The combined framework regions of the constituent light and heavy chains serve to position and align the CDRs. The CDRs are primarily responsible for binding to an epitope of an antigen and are typically referred to as CDR1, CDR2, and CDR3, numbered sequentially starting from the N-terminus of the variable region chain. Framework regions are similarly numbered.

The general arrangement of T cell receptor genes is similar to that of antibody heavy chains, T cell receptors (TCR) have both variable domains (V) and constant (C) domains. The V domains function to bind antigen. There are regions in the V domain homologous to the framework CDR regions of antibodies. Homology to the immunoglobulin V regions can be determined by alignment. The V region of the TCRs has a high amino acid sequence homology with the Fv of antibodies. Hedrick et al., *Nature* (London) 308:153–158 (1984), incorporated by reference herein.

The term CDR, as used herein, refers to amino acid sequences which together define the binding affinity and specificity of the natural variable binding region of a native immunoglobulin binding site (such as FV), a T cell receptor (such as $V_\alpha$ and $V_\beta$), or a synthetic polypeptide which mimics this function. The term "framework region" or "FR", as used herein, refers to amino acid sequences interposed between CDRs.

The "ligand binding moieties" referred to here are those molecules that have a variable domain that is capable of functioning to bind specifically or otherwise recognize a particular ligand or antigen. Moieties of particular interest include antibodies and T cell receptors, as well as synthetic or recombinant binding fragments of those such as Fv, Fab, F(ab')$_2$ and the like. Appropriate variable regions include $V_H$, $V_L$, $V_\alpha$ and $V_\beta$ and the like.

Practice of this invention preferably employs the Fv portions of an antibody or the V portions of a TCR only. Other sections, e.g., $C_H$ and $C_L$, of native immunoglobulin protein structure need not be present and normally are intentionally omitted from the polypeptides of this invention. However, the polypeptides of the invention may comprise additional polypeptide regions defining a bioactive region, e.g., a toxin or enzyme, or a site onto which a toxin or a remotely detectable substance can be attached, as will be described below.

Preparation of Fv Fragments

Information regarding the Fv antibody fragments or other ligand binding moiety of interest is required in order to produce proper placement of the disulfide bond to stabilize the desired disulfide stabilized fragment, such as an Fv fragment (dsFv). The amino acid sequences of the variable fragments that are of interest are compared by alignment with those analogous sequences in the well-known publication by Kabat and Wu, supra, to determine which sequences can be mutated so that cysteine is encoded for in the proper position of each heavy and light chain variable region to provide a disulfide bond in the framework regions of the desired polypeptide fragment. Cysteine residues are necessary to provide the covalent disulfide bonds. For example, a disulfide bond could be placed to connect FR4 of $V_L$ and FR2 of $V_H$; or to connect FR2 of $V_L$ and FR4 of $V_H$.

After the sequences are aligned, the amino acid positions in the sequence of interest that align with the following positions in the numbering system used by Kabat and Wu are identified: positions 43, 44, 45, 46, and 47 (group 1) and positions 103, 104, 105, and 106 (group 2) of the heavy chain variable region; and positions 42, 43, 44, 45, and 46 (group 3) and positions 98, 99, 100, and 101 (group 4) of the light chain variable region. In some cases, some of these positions may be missing, representing a gap in the alignment.

Then, the nucleic acid sequences encoding the amino acids at two of these identified positions are changed such that these two amino acids are mutated to cysteine residues. The pair of amino acids to be selected are, in order of decreasing preference:

$V_H44$-$V_L100$,
$V_H105$-$V_L43$,
$V_H105$-$V_L42$,
$V_H44$-$V_L101$,
$V_H106$-$V_L43$,
$V_H104$-$V_L43$,
$V_H44$-$V_L99$,
$V_H45$-$V_L98$,
$V_H46$-$V_L98$,
$V_H103$-$V_L43$,
$V_H103$-$V_L44$,
$V_H103$-$V_L45$.

Most preferably, substitutions of cysteine are made at the positions:

$V_H44$-$V_L100$; or
$V_H105$-$V_L43$.

(The notation $V_H44$-$V_L100$, for example, refers to a polypeptide with a $V_H$ having a cysteine at position 44 and a cysteine in $V_L$ at position 100; the positions being in accordance with the numbering given by Kabat and Wu.)

Note that with the assignment of positions according to Kabat and Wu, the numbering of positions refers to defined conserved residues and not to actual amino acid positions in a given antibody. For example, CysL100 (of Kabat and Wu) which is used to generate ds(Fv)B3 as described in the example below, actually corresponds to position 105 of B3($V_L$).

In the case of $V_\alpha$ and $V_\beta$ of T cell receptors, reference can also be made to the numbering scheme in Kabat and Wu for T cell receptors. Substitutions of cysteines can be made at position 41, 42, 43, 44 or 45 of $V_\alpha$ and at position 106, 107, 108, 109 or 110 of $V_\beta$; or at position 104, 105, 106, 107, 108 or 109 of $V_\alpha$ and at position 41, 42, 43, 44 or 45 of $V_\beta$, such positions being in accordance with the Kabat and Wu numbering scheme for TCRs. When such reference is made, the most preferred cysteine substitutions are $V_\alpha42$-$V_\beta110$ and $V_\alpha108$-$V_\beta42$. $V_\beta$ positions 106, 107 and $V_\alpha$ positions 104, 105 are CDR positions, but they are positions in which disulfide bonds can be stably located.

As an alternative to identifying the amino acid position for cysteine substitution with reference to the Kabat and Wu numbering scheme, one could align a sequence of interest with the sequence for monoclonal antibody (MAb) B3 (see below) set out in FIG. 1. The amino acid positions of B3 which correlate with the Kabat and Wu $V_H$ positions set forth above for Group 1 are 43, 44, 45, 46, and 47, respectively; for Group 2 are 109, 110, 111, and 112, respectively. The amino acid positions of B3 which correlate with the Kabat and Wu $V_L$ positions set forth above for Group 3 are 47, 48, 49, 50 and 51, respectively; Group 4 are 103, 104, 105, and 106, respectively.

Alternatively, the sites of mutation to the cysteine residues can be identified by review of either the actual antibody or the model antibody of interest as exemplified below. Computer programs to create models of proteins such as antibodies are generally available and well-known to those skilled in the art (see Kabat and Wu; Loew, et al., *Int. J. Quant. Chem., Quant. Biol. Symp.*, 15:55–66 (1988) Bruccoleri, et al., *Nature*, 335:564–568 (1988); Chothia, et al., *Science*, 233:755–758 (1986), all of which are incorporated herein by reference. Commercially available computer programs can be used to display these models on a computer monitor, to calculate the distance between atoms, and to estimate the likelihood of different amino acids interacting (see, Ferrin, et al., *J. Mol. Graphics*, 6:13–27 (1988), incorporated by reference herein. For example, computer models can predict charged amino acid residues that are accessible and relevant in binding and then conformationally restricted organic molecules can be synthesized. See, for example, Saragovi, et al., *Science*, 253:792 (1991), incorporated by referenced herein. In other cases, an experimentally determined actual structure of the antibody may be available.

A pair of suitable amino acid residues should (1) have a $C_\alpha$—$C_\alpha$ distance between the two residues less than or equal to 8 Å, preferably less than or equal to 6.5 Å (determined from the crystal structure of antibodies which are available such as those from the Brookhaven Protein Data Bank) and (2) be as far away from the CDR region as possible. Once they are identified, they can be substituted with cysteines. The $C_\alpha$—$C_\alpha$ distances between residue pairs in the modeled B3 at positions homologous to those listed above are set out in Table 1, below.

Introduction of one pair of cysteine substitutions will be sufficient for most applications. Additional substitutions may be useful and desirable in some cases.

Modifications of the genes to encode cysteine at the target point may be readily accomplished by well-known techniques, such as site-directed mutagenesis (see, Gillman and Smith, *Gene,* 8:81–97 (1979) and Roberts, S., et al, *Nature,* 328:731–734 (1987), both of which are incorporated herein by reference) by the method described in Kunkel, *Proc. Natl. Acad Sci. USA* 82:488–492 (1985), incorporated by reference herein, or by any other means known in the art.

Separate vectors with sequences for the desired $V_H$ and $V_L$ sequences (or other homologous V sequences) may be made from the mutagenized plasmids. The sequences encoding the heavy chain regions and the light chain regions are produced and expressed in separate cultures in any manner known or described in the art, with the exception of the guidelines provided below. If another sequence, such as a sequence for a toxin, is to be incorporated into the expressed polypeptide, it can be linked to the $V_H$ or the $V_L$ sequence at either the N- or C-terminus or be inserted into other protein sequences in a suitable position. For example, for *Pseudomonas exotoxin* (PE) derived fusion proteins, either $V_H$ or $V_L$ should be linked to the N-terminus of the toxin or be inserted into domain III of PE, like for example TGF$\alpha$ in Theuer et al., *J. Urology* 149 (1993), incorporated by reference herein. For Diphtheria toxin-derived immunotoxins, $V_H$ or $V_L$ is preferably lined to the C-terminus of the toxin.

Peptide linkers, such as those used in the expression of recombinant single chain antibodies, may be employed to link the two variable regions ($V_H$ and $V_L$, $V_\alpha$ and $V_\beta$) if desired and may positively increase stability in some molecules. Bivalent or multivalent disulfide stabilized polypeptides of the invention can be constructed by connecting two or more, preferably identical, $V_H$ regions with a peptide linker and adding $V_L$ as described in the examples, below. Connecting two or more $V_H$ regions by linkers is preferred to connecting $V_L$ regions by linkers since the tendency to form homodimers is greater with $V_L$ regions. Peptide linkers and their use are well-known in the art. See, e.g., Huston et al., *Proc. Natl. Acad. Sci., USA,* supra; Bird et al., *Science,* supra; Glockshuber et al., supra; U.S. Pat. No. 4,946,778, U.S. Pat. No. 5,132,405 and most recently in Stemmer et al., *Biotechniques* 14:256–265 (1993), all incorporated herein by reference.

Proteins of the invention can be expressed in a variety of host cells, including *E. coli,* other bacterial hosts, yeast, and various higher eucaryotic cells such as the COS, CHO and HeLa cells lines and myeloma cell lines. The recombinant protein gene will be operably linked to appropriate expression control sequences for each host. For *E. coli* this includes a promoter such as the T7, trp, tac, lac or lambda promoters, a ribosome binding site, and preferably a transcription terminal signal. For eucaryotic cells, the control sequences will include a promoter and preferably an enhancer derived from immunoglobulin genes, SV40, cytomegalovirus, etc., and a polyadenylation sequence, and may include splice donor and acceptor sequences. The plasmids of the invention can be transferred into the chosen host cell by well-known methods such as calcium chloride transformation for *E. coli* and calcium phosphate treatment or electroporation for mammalian cells. Cells transformed by the plasmids can be selected by resistance to antibiotics conferred by genes contained on the plasmids, such as the amp, gpt, neo and hyg genes.

Methods for expressing of single chain antibodies and/or refolding to an appropriate folded form, including single chain antibodies, from bacteria such as *E. coli* have been described and are well-known and are applicable to the polypeptides of this invention. See, Buchner et al., *Analytical Biochemistry* 205:263–270 (1992); Pluckthun, *Biotechnology,* 9:545 (1991); Huse, et al., *Science,* 246:1275 (1989) and Ward, et al., *Nature,* 341:544 (1989), all incorporated by reference herein.

Often, functional protein from *E. coli* or other bacteria is generated from inclusion bodies and requires the solubilization of the protein using strong denaturants, and subsequent refolding. In the solubilization step, a reducing agent must be present to dissolve disulfide bonds as is well-known in the art. An exemplary buffer with a reducing agent is: 0.1 M Tris, pH8, 6M guanidine, 2 mM EDTA, 0.3 M DTE (dithioerythritol). Reoxidation of protein disulfide bonds can be effectively catalyzed in the presence of low molecular weight thiol reagents in reduced and oxidized form, as described in Saxena et al., *Biochemistry* 9: 5015–5021 (1970), incorporated by reference herein, and especially described by Buchner, et al., *Anal. Biochem.,* supra (1992).

Renaturation is typically accomplished by dilution (e.g. 100-fold) of the denature and reduced protein into refolding buffer. An exemplary buffer is 0.1 M Tris, pH8.0, 0.5 M L-arginine, 8 mM oxidized glutathione (GSSG), and 2 mM EDTA.

As a necessary modification to the single chain antibody protocol, the heavy and light chain regions were separately solubilized and reduced and then combined in the refolding solution. A preferred yield is obtained when these two proteins are mixed in a molar ratio such that a molar excess of one protein over the other does not exceed a 5 fold excess.

It is desirable to add excess oxidized glutathione or other oxidizing low molecular weight compounds to the refolding solution after the redox-shuffling is completed.

Purification of Polypeptides

Once expressed, the recombinant proteins can be purified according to standard procedures of the art, including ammonium sulfate precipitation, affinity columns, column chromatography, and the like (see, generally, R. Scopes, *Protein Purification,* Springer-Verlag, N.Y. (1982)). Substantially pure compositions of at least about 90 to 95% homogeneity are preferred, and 98 to 99% or more homogeneity are most preferred for pharmaceutical uses. Once purified, partially or to homogeneity as desired, the polypeptides should be substantially free of endotoxin for pharmaceutical purposes and may then be used therapeutically.

Various dsFv Fragment Molecules

It should be understood that the description of the dsFv peptides described above can cover all classes/groups of antibodies of all different species (e.g., mouse, rabbit, goat, human) chimeric peptides, humanized antibodies and the like. "Chimeric antibodies" or "chimeric peptides" refer to those antibodies or antibody peptides wherein one portion of the peptide has an amino acid sequence that is derived from, or is homologous to, a corresponding sequence in an antibody or peptide derived from a first gene source, while the remaining segment of the chain(s) is homologous to corresponding sequences of another gene source. For example, chimeric antibodies can include antibodies where the framework and complementarity determining regions are from different sources. For example, non-human CDRs are integrated into human framework regions linked to a human constant region to make "humanized antibodies." See, for example, PCT Application Publication No. WO 87/02671, U.S. Pat. No. 4,816,567, EP Patent Application 0173494, Jones, et al., *Nature*, 321:522–525 (1986) and Verhoeyen, et al., *Science*, 239:1534–1536 (1988), all of which are incorporated by reference herein. Similarly, the source of $V_H$ can differ from the source of $V_L$.

The subject polypeptides can be used to make fusion proteins such as immunotoxins. Immunotoxins are characterized by two functional components and are particularly useful for killing selected cells in vitro or in vivo. One functional component is a cytotoxic agent which is usually fatal to a cell when attached or absorbed to the cell. The second functional component, known as the "delivery vehicle," provides a means for delivering the toxic agent to a particular cell type, such as cells comprising a carcinoma. The two components can be recombinantly fused together via a peptide linker such as described in Pastan et al., *Ann. Rev. Biochem.* (1992), infra. The two components can also be chemically bonded together by any of a variety of well-known chemical procedures. For example, when the cytotoxic agent is a protein and the second component is an intact immunoglobulin, the linkage may be by way of heterobifunctional cross-liners, e.g., SPDP, carbodiimide, or the like. Production of various immunotoxins is well-known within the art, and can be found, for example in "Monoclonal Antibody-Toxin Conjugates: Aiming the Magic Bullet," Thorpe et al., *Monoclonal Antibodies in Clinical Medicine*, Academic Press, pp. 168–190 (1982) and Waldmann, *Science*, 252:1657 (1991), both of which are incorporated herein by reference.

A variety of cytotoxic agents are suitable for use in immunotoxins. Cytotoxic agents can include radionuclides, such as Iodine-131, Yttrium-90, Rhenium-188, and Bismuth-212; a number of chemotherapeutic drugs, such as vindesine, methotrexate, adriamycin, and cisplatin; and cytotoxic proteins such as ribosomal inhibiting proteins like pokeweed antiviral protein, Pseudomonas exotoxin A, ricin, diphtheria toxin, ricin A chain, gelonin, etc., or an agent active at the cell surface, such as the phospholipase enzymes (e.g., phospholipase C). (See, generally, Pastan et al., "Recombinant Toxins as Novel Therapeutic Agents," *Ann. Rev. Biochem.* 61:331–354 (1992); "Chimeric Toxins," Olsnes and Phil, *Pharmac. Ther.*, 25:355–381 (1982), and "Monoclonal Antibodies for Cancer Detection and Therapy," eds. Baldwin and Byers, pp. 159–179, 224–266, Academic Press (1985), which are incorporated herein by reference.)

The polypeptides can be conjugated or recombinantly fused to a variety of pharmaceutical agents in addition to those described above, such as drugs, enzymes, hormones, chelating agents capable of binding an isotope, catalytic antibodies and other proteins useful for diagnosis or treatment of disease.

For diagnostic purposes, the polypeptides can either be labeled or unlabeled. A wide variety of labels may be employed, such as radionuclides, fluors, enzymes, enzyme substrates, enzyme cofactors, enzyme inhibitors, ligands (particularly haptens), and the like. Numerous types of immunoassays are available and are well known to those skilled in the art.

Molecules Homologous to Antibody Fv Domains—T-cell Receptors

This invention can apply to molecules that exhibit a high degree of homology to the antibody Fv domains, including the ligand-specific V-region of the T-cell receptor (TCR). An example of such an application is outlined below. The sequence of the antigen-specific V region of a TCR molecule, 2B4 (Becker et. al., *Nature* (London) 317:430–434 (1985)), was aligned against the Fv domains of two antibody molecules McPC603 (see below) and J539 (Protein Data Bank entry 2FBJ), using a standard sequence alignment package. When the $V_\alpha$ sequence of 2B4 was aligned to the $V_H$ sequences of the two antibodies, the S1 site residue, corresponding to $V_H44$ to B3, can be identified as $V_\alpha 43S$ (TCR 42 in the numbering scheme of Kabat and Wu) and the S2 site residue, corresponding to $V_H111$ of B3, and $V_\alpha 104Q$ (TCR 108 in the number scheme of Kabat and Wu). When the same $V_\alpha$ sequence was aligned to the $V_L$ sequences of the two antibodies, the same residues, $V_\alpha 43S$ and $V_\alpha 104Q$, can be identified, this time aligned to the residues corresponding to $V_L 48$ and $V_L 105$ of B3, respectively. Similarly, the 2B4 residues $V_\beta 42E$ and $V_\beta 107P$ (TCR 42 and 110 in the numbering scheme of Kabat, et al.) can be aligned to antibody residues corresponding to $V_H 44$ and $V_H 111$ of B3 and at the same time to $V_L 48$ and $V_L 105$ of B3. Therefore, the two most preferred interchain disulfide bond sites in this TCR are $V_\alpha 43$-$V_\beta 107$ and $V_\alpha 104$-$V_\beta 42$. Mutating the two residues in one of these pairs of residues into cysteine will introduce a disulfide bond between and α and β chains of this molecule. The stabilization that results from this disulfide bond will make it possible to isolate and purify these molecules in large quantities.

Binding Affinity of dsFv Polypeptides

The polypeptides of this invention are capable of specifically binding a ligand. For this invention, a polypeptide specifically binding a ligand generally refers to a molecule capable of reacting with or otherwise recognizing or binding antigen or to a receptor on a target cell. An antibody or other polypeptide has binding affinity for a ligand or is specific for a ligand if the antibody or peptide binds or is capable of binding the ligand as measured or determined by standard antibody-antigen or ligand-receptor assays, for example, competitive assays, saturation assays, or standard immunoassays such as ELISA or RIA. This definition of specificity applies to single heavy and/or light chains, CDRs, fusion proteins or fragments of heavy and/or light chains, that are specific for the ligand if they bind the ligand alone or in combination.

In competition assays the ability of an antibody or peptide fragment to bind a ligand is determined by detecting the ability of the peptide to compete with the binding of a compound known to bind the ligand. Numerous types of competitive assays are known and are discussed herein. Alternatively, assays that measure binding of a test compound in the absence of an inhibitor may also be used. For instance, the ability of a molecule or other compound to bind the ligand can be detected by labelling the molecule of interest directly or the molecule be unlabelled and detected indirectly using various sandwich assay formats. Numerous types of binding assays such as competitive binding assays are known (see, e.g., U.S. Pat. Nos. 3,376,110, 4,016,043, and Harlow and Lane, *Antibodies: A Laboratory Manual*, Cold Spring Harbor Publications, N.Y. (1988), which are incorporated herein by reference). Assays for measuring binding of a test compound to one component alone rather than using a competition assay are also available. For instance, immunoglobulin polypeptides can be used to identify the presence of the ligand. Standard procedures for monoclonal antibody assays, such as ELISA, may be used (see, Harlow and Lane, supra). For a review of various signal producing systems which may be used, see, U.S. Pat. No. 4,391,904, which is incorporated herein by reference.

The following examples are offered for the purpose of illustration and are not to be construed as limitations on the invention.

EXAMPLES

The computer modeling and identification of residues in the conserved framework regions of $V_H$ and $V_L$ of the monoclonal antibody (MAb) B3 and MAb e23 that can be mutated to cysteines and form a disulfide-stabilized Fv without interfering with antigen binding are disclosed. B3 reacts with specific carbohydrates present on many human cancers. (Pastan et al., *Cancer Res.* 51:3781–3787 (1991), incorporated by reference herein.) MAb e23 reacts specifically with the erbB2 antigen present on many human carcinomas. Active immunotoxins containing such as disulfide-stabilized Fv are also described.

I. Design of a disulfide connection between $V_H$ and $V_L$ of MAb B3 which does not affect the structure of the binding site.

A. Design Approach

Because the tertiary structure of MAb B3 is not known, we generated a model of B3 (Fv) from the structure of MAb McPC603 (see below) by replacing or deleting appropriate amino acids. MAb McPC603 was selected because it has the highest overall (L+H) sequence identity and similarity among all published mouse antibody structures. A total of 44 (including 2 deletions) and 40 (including 1 deletion) amino acids of the $V_H$ and $V_L$ domains, respectively, of McPC603 were changed. No insertion was necessary. This structure was then energy-minimized using CHARMM (see below) in stages; first only hydrogen atoms were varied, then the deleted regions, then all the mutated residues, and finally the whole molecule.

Three criteria were used to select possible positions for disulfide-connections between $V_H$ and $V_L$. (i) The disulfide should connect amino acids in structurally conserved framework regions of $V_H$ and $V_L$, so that the disulfide stabilization works not only for B3 (Fv) but also for other Fvs. (ii) The distance between $V_H$ and $V_L$ should be small enough to enable the formation of a disulfide without generating strain on the Fv structure. (iii) The disulfide should be at a sufficient distance from the CDRs to avoid interference with antigen binding. These criteria were met by the following two potential disulfide bridges, although there are other potential sites around the two sites as shown in Table 1. One possibility was to replace Arg44 of B3 ($V_H$) and Ser105 of B3 ($V_L$) with cysteines to generate a disulfide between those positions. The other was to change Gln111 of B3 ($V_H$) and Ser48 of B3 ($V_L$) to cysteines (See FIG. 1). These two pairs are related to one another by the pseudo two-fold symmetry that approximately relates the $V_H$ and $V_L$ structures. In each case, one of the residues involved in the putative disulfide bond ($V_H$111,$V_L$105) is flanked on both sides by a highly conserved Gly residue which can help absorb local distortions to the structure caused by the introduction of the disulfide bond. We energy-minimized models for both possibilities as well as one in which both disulfide bonds are present. The $V_H$44-$V_L$105 connection was chosen for further study because the energy-refined model structure with this connection had a slightly better disulfide bond geometry than that with the $V_H$111-$V_L$48 connection. With some other antibodies this latter connection may be preferable over the former.

B. Computer Modeling

The initial model of the B3 (Fv) structure was obtained from the structure of the variable domain of McPC603 (Satow et al., *J. Mol. Biol.* 190:593–604 (1986)), Brookhaven Protein Data Bank (Brookhaven National Laboratory, Upton, Long Island, N.Y.) entry 1MCP, (Abola et al., *Crystallographic Databases-Information Content, Software Systems, Scientific Applications* pp. 107–132 (1987)) be deletion and mutation of appropriate residues using an in-house molecular graphics program known as GEMM. The structure of this model and those of various mutants were refined by a series of the adopted basis set Newton Ralphson (ABNR) energy minimization procedure using the molecular dynamics simulation program CHARMM (as described in Brooks et al., *J. Comp. Chem.* 4:187–217 (1983), incorporated by reference herein) version 22. Details of this procedure are as follows:

1. Energy Minimization

All structural refinements were performed by the ABNR (adopted basis set Newton Ralphson) energy minimization procedure using the molecular dynamics simulation program CHARMM (Brooks et al., supra), version 22. All-H parameter set was used; nonbond cutoff distance was 13.0 Å, with switching function applied to the Lennard-Jones potential and shifting function to the electrostatic interactions between 10 and 12 Å. Solvent was not included. The dielectric constant of 1 was used for all refinements except for the last runs, for which a distance-dependent dielectric constant was used.

2. Construction of the Wild-Type B3 Fv Model

A model of the B3 Fv structure was first obtained from the structure of the Fv domain of McPC603 (Satow et al., supra; Protein Data Bank entry 1MCP, Abola et al., supra) by deletion and mutation of appropriate residues using a molecular graphics program GEMM. The sequence alignment scheme used to find corresponding residues was that of Kabat and Wu (supra, FIG. 1). The McPC603 structure was chosen over other known mouse Fab structures (e.g., J539 and R19.9, Protein Data Bank entries 2FBJ and 2F19, respectively) because its Fv portion has the highest overall identity and similarity in the amino acid sequence with that of B3. A total of 44 (including two deletions) and 40 (including one deletion) amino acids of the $V_H$ and $V_L$ domains, respectively, of McPC603 were changed, but no insertion was needed.

This initial structure was then refined according to the following protocol: (1) Hydrogen atoms (both polar and nonpolar) were added using CHARMM and their positions refined by a 50-step energy minimization with the heavy atoms fixed. (2) In order to allow the C—N bond length reduction around the deletion regions, a 20-step energy minimization was done with all atoms fixed except those for 10 amino acids around each of the three deletion regions ($V_L$:28–37, $V_H$:50–59, 99–108), which were constrained with mass-weighted harmonic force of 20 kcal/mol/Å. This minimization was repeated with the harmonic constraint force of 15, 10, and then 5 kcal/mol/Å, each for 20 steps. (3) The same set of constrained minimizations of step (2) was repeated using an expanded list of variable amino acids to include all the mutated amino acids as well as the 30 amino acids around the deletion regions. (4) Finally, the same set of constrained minimizations was repeated to refine all atoms in the structure. The structure obtained after this set of refinements served as the starting structure for the disulfide bond introduction between $V_H$ and $V_L$ domains and for the Ser to Tyr mutation (see below). The final structure of the wild-type B3 Fv was obtained after two additional sets of energy minimizations using a distance-dependent dielectric constant (see below).

3. Construction of the Tyr Mutant Model

During the examination of the newly constructed structure of B3 Fv, it was noted that there was an empty concave space in the $V_H$-$V_L$ interface region of the FR core of the B3 Fv model structure, near the Ser side chain at $V_H 95$ position ($V_H 91$ in Kabat and Wu, supra). Other crystal structures of Fab have either Tyr or Phe at the corresponding position. The sequence data in Kabat et al. (supra) also show that this position is most often occupied by either Tyr or Phe. Thus, Ser at this position in B3 appears to be an anomaly. Furthermore, it was apparent from visual inspection that the side chain of Tyr at this position would fill the nearby empty space very nicely with hardly any change at all in the rest of the structure and that this would promote the $V_H$-$V_L$ association by enhancing the hydrophobic and van der Waals interactions. We, therefore, constructed and energy-refined the Tyr mutant structure.

The protocol used to construct the Tyr mutant model was similar to that used to construct the B3 Fv model: (1) The Ser residue of $V_H$ was replaced by Tyr using GEMM. (2) Hydrogen atoms were added and their positions refined using CHARMM by a 20-step energy minimization with all other atoms fixed. (3) all atoms of the new Tyr residue were allowed to vary during the next 20-step minimization with all other atoms fixed. (4) Finally, all atoms of the structure were allowed to relax in stages by means of four successive sets of 20-step energy minimization, each set with the mass-weighted harmonic constraint force of 20, 15, 10, and then 5 kcal/mol/Å.

4. Selection of Possible Disulfide Bond Position Between $V_H$ and $V_L$ Domains Possible mutation sites for the introduction of a disulfide bond between the $V_H$ and $V_L$ domains were initially identified by visual inspection of the initial model of B3 using our molecular graphics program, GEMM. The criteria for selection were, (1) that both of the pair of residues to be mutated to Cys be in the FR-region of the molecule, at least one residue away from the CDRs in the primary sequence and (2) that the $C_\alpha$—$C_\alpha$ distance between the two residues be less than or equal to 6.5 Å. Two pairs could be identified: $V_H 44R$-$V_L 105S$ and $V_H 111Q$-$V_L 48S$. After the B3 model structure had been fully refined, the program CHARMM was used to systematically search for all residue pairs between the FR regions of $V_H$ and $V_L$ domains, for which the $C_\alpha$—$C_\alpha$ distance was less than a specified value. The result of this search is summarized in Table 1, which shows that the $C_\alpha$—$C_\alpha$ distance is the shortest at the two sites identified with the initial model of B3, but that other sites exist that are also potential candidates.

TABLE 1

All $C_\alpha$—$C_\alpha$ distances (in Angstroms) less than or equal to 8.0 Å between the FR regions of $V_H$ and $V_L$ of the Fv B3 model structure.

| | | | |
|---|---|---|---|
| $V_H 43$–$V_L 105$ | 8.0 | $V_L 47$–$V_H 111$ | 6.9 |
| $V_H 44$–$V_L 103$ | 7.5 | $V_L 47$–$V_H 112$ | 8.0 |
| $V_H 44$–$V_L 104$ | 7.2 | $V_L 48$–$V_H 95$ | 7.4 |
| $V_H 44$–$V_L 105$ | 5.7 | $V_L 48$–$V_H 109$ | 7.0 |
| $V_H 44$–$V_L 106$ | 6.4 | $V_L 48$–$V_H 110$ | 6.8 |
| $V_H 45$–$V_L 103$ | 6.0 | $V_L 48$–$V_H 111$ | 5.6 |
| $V_H 45$–$V_L 104$ | 7.7 | $V_L 48$–$V_H 112$ | 6.5 |
| $V_H 45$–$V_L 105$ | 8.0 | $V_L 49$–$V_H 109$ | 7.0 |
| $V_H 46$–$V_L 102$[a] | 7.3 | $V_L 50$–$V_H 108$[a] | 7.5 |
| $V_H 46$–$V_L 103$ | 6.9 | $V_L 50$–$V_H 109$ | 6.9 |
| $V_H 47$–$V_L 101$[a] | 6.4 | $V_L 51$–$V_H 107$[a] | 7.0 |

TABLE 1-continued

All $C_\alpha$—$C_\alpha$ distances (in Angstroms) less than or equal to 8.0 Å between the FR regions of $V_H$ and $V_L$ of the Fv B3 model structure.

| | |
|---|---|
| $V_H 47$–$V_L 102$[a] | 6.8 |
| $V_H 47$–$V_L 103$ | 7.8 |

[a]These residues are in the CDR region, but have close proximity to the FR region.

$V_H$ positions 43, 101 and 102 and $V_L$ positions 96 and 97 are located in the CDR region, but do yield stable ds bonds when substituted with cysteines, while maintaining binding specificity.

5. Construction of the Disulfide-Bonded B3 Fv Models

Once these potential disulfide bond sites were identified, six disulfide bonded models were generated. Three of these were "s44" (B3 Fv with $V_H 44R$ and $V_L 105S$ changed to Cys and disulfide bonded), "s111" (B3 Fv with $V_H 111Q$ and $V_L 48S$ changed to Cys and disulfide bonded), and "s44,111" (B3 Fv with both disulfide bonds). The other three were the corresponding disulfide bonded forms of the Tyr mutant, B3 yFv. These are labelled as y44, y111, and y44,111. All six model structures were refined by energy minimization using an identical protocol. This consisted of (1) mutation of the appropriate residues using GEMM, (2) addition of the hydrogen atoms, (3) allowing the disulfide bond(s) to form by relaxing the Cys residues and the two neighboring Gly residues by a 100-step energy minimization with all other atoms fixed, (4) refinement of all atoms of the structure by four successive sets of 20-step energy minimizations, each with the mass—weighted harmonic constraint force of 20, 15, 10, and then 5 kcal/mol/Å. Afterwards, all structures were subjected to the final refinements as described below.

6. Generation of the Final Models of the Wild-Type and Different Variants of B3 Fv The constructed models of B3 Fv and of all of its variants were subjected to an additional 500-step minimization followed by another 500-step procedure with the exit criterion being to stop the run when the total energy change becomes less than or equal to 0.01 kcal/mol. These final calculations were carried out without any constraint and using the distance-dependent dielectric constant. The various energy values reported in Table 2 are from the last cycle of these calculations.

TABLE 2

The energy components, in kcal/mol, of B3 $F_v$, of the species with an interchain disulfide bond at $V_H 44$–$V_L 105$ (s44), at $V_H 111$–$V_L 48$ (s111), at both sites (s44, 111), and of their corresponding variants with Ser to Tyr mutation at $V_H 95$ (B3 yFv, y44, y111, and y44, 111).

| | B3 Fv | s44 | s111 | s44, 111 |
|---|---|---|---|---|
| S1[a] | −35.4 | 33.8 | −35.2 | 34.6 |
| S2[b] | 23.4 | 23.5 | 39.8 | 39.7 |
| R[c] | −893.9 | −909.7 | −826.6 | −833.0 |
| S1-R[d] | −65.1 | −25.9 | −64.5 | −25.5 |
| S2-R[e] | −58.6 | −58.8 | −29.4 | −29.5 |
| $V_H$–$V_L$[f] | −172.1 | −150.4 | −150.5 | −116.9 |
| Total[g] | −1029.6 | −937.1 | −915.9 | −813.7 |

| | B3 yFv | y44 | y111 | y44, 111 |
|---|---|---|---|---|
| S1[a] | −35.1 | 33.9 | −35.3 | 33.4 |

TABLE 2-continued

The energy components, in kcal/mol, of B3
$F_v$, of the species with an interchain disulfide bond at
$V_H44$–$V_L105$ (s44), at $V_H111$–$V_L48$ (s111), at both sites
(s44, 111), and of their corresponding variants with Ser to Tyr
mutation at $V_H95$ (B3 yFv, y44, y111, and y44, 111).

| S2[b] | 23.8 | 22.7 | 40.4 | 39.9 |
|---|---|---|---|---|
| R[c] | −910.1 | −943.3 | −902.6 | −912.0 |
| S1-R[d] | −66.0 | −26.4 | −65.2 | −26.2 |
| S2-R[e] | −63.8 | −74.5 | −33.2 | −33.1 |
| $V_H$–$V_L$[f] | −192.6 | −161.3 | −177.6 | −141.6 |
| Total[g] | −1051.2 | −987.6 | −996.0 | −898.1 |

[a]Residues $V_H44$ (R or C) and $V_L105$ (S or C).
[b]Residues $V_H111$ (Q or C) and $V_L48$ (S or C).
[c]Rest of the molecule other than S1 and S2.
[d]Interaction energy between groups S1 and R.
[e]Interaction energy between groups S2 and R.
[f]Interaction energy between $V_H$ and $V_L$.
[g]Sum of the energies for S1, S2, R, S1-R, and S2-R, plus the interaction energy between S1 and S2, which is negligible for all molecules.

7. Model of B3 Fv Fragment

The refined model of B3 Fv structure can be compared to the (unrefined) crystal structure of McPC603 (not shown). The rms deviations between the $C_\alpha$ atoms of these two structures, excluding the deleted residues, were 0.75, 1.18, and 0.91 Å, respectively, for the FR-region, CDR-region, and the whole molecule. Most of the difference occurs at the loops and at the C- and N-terminals of the molecule. Some of the difference between these structures is probably also due to the fact that one is energy-refined and the other not. The McPC603 structure was not refined because an energy-minimized structure is not necessarily more reliable than the crystal structure, especially when the refinements are carried out without the solvent water.

8. Tyr Mutant of B3 Fv (B3 yFv)

As described above, we constructed a mutant of B3 Fv wherein the Ser residue at $V_H95$ is replaced by a Tyr residue. The effect of this mutation upon the stability of Fv cannot be computed quantitatively because of the lack of information on the structure of the dissociated, unfolded form of Fv. The numbers that are produced naturally during the structure refinement are various energy terms in the folded form of the molecule. When the Ser side chain was replaced by that of Tyr, the Lennard-Jones potential energy of the mutated residue with the rest of the protein was 1.79 kcal/mol before the hydrogen atoms were refined, 0.05 kcal/mol after a 20-step of minimization of the hydrogen atoms only, and −20 kcal/mole after full refinement of all atoms. These numbers indicate that the modeled B3 Fv structure can accommodate a Tyr residue at this position without any serious steric overlap. The various energy terms after full refinement of all atoms are listed in Table 2. It can be seen that the Tyr mutant always has lower energy than its Ser counterpart, both in the wild-type and in all of the Cys mutants. The rms deviation between the main-chain atoms of B3 Fv and B3 yFv was 0.15 Å.

9. Models of Disulfide Bonded B3 Fv Fragments

The two sites selected for a potential inter-chain disulfide bond formation are site S1 at $V_H44R$-$V_L105S$ and site S2 at $V_H111Q$-$V_L48S$ ($V_H44$-$V_L100$ and $V_H105$-$V_L43$, respectively, according to the numbering scheme of Kabat et al., supra). These sites are in the FR region, at least two residues away from the nearest CDR region. The inter-chain $C_\alpha$–$C_\alpha$ distance was the shortest in the unrefined model and is the shortest in the refined model (Table 1). It was also noted that one of the residues in each pair, $V_L105$ and $V_H111$, is flanked on both sides by a highly conserved Gly residue. We reasoned that these Gly residues would provide flexibility to the middle residue and absorb some of the distortions that could be produced when a disulfide bond is formed.

We constructed both the singly and doubly disulfide bonded models, each with or without the Ser to Tyr mutation at $V_H95$. The structural change upon introduction of the disulfide bond is small if computed as an average per residue - the rms deviations between the main-chain atoms of the disulfide bonded variants and those of their parent molecules were 0.2 to 0.3 Å. However, significant changes do occur at the site of mutation as is inevitable since the $C_\alpha$–$C_\alpha$ distance must decrease by 0.5 to 1.0 Å. (See Tables 1 and 3.) Large changes, however, appear to propagate only a short distance along the chain and all but disappear within a couple of residues or after the first loop in the FR region.

TABLE 3

The values of the dihedral angle (in degrees) and of the $C_\alpha$–$C_\alpha'$ distance (in Å) of the cysteine residue in various species[a]

|  | $C_\alpha$–$C_\beta$ | $C_\beta$–S | S–S' | S'–$C_\beta'$ | $C_\beta'$–$C_\alpha'$ | $C_\alpha$–$C_\alpha'$ |
|---|---|---|---|---|---|---|
| S1 ($V_H44$–$V_L105$): | | | | | | |
| s44 | −48.4 | −143.0 | 93.9 | −89.6 | −76.2 | 4.66 |
| s44, 111 | −41.9 | −150.2 | 95.9 | −87.1 | −76.8 | 4.76 |
| y44 | −49.1 | −142.3 | 93.7 | −87.5 | −76.4 | 4.59 |
| y44, 111 | −49.3 | −138.8 | 92.4 | −93.1 | −73.8 | 4.63 |
| S2 ($V_L48$–$V_H111$): | | | | | | |
| s111 | 35.0 | 179.5 | 68.5 | −90.9 | −74.1 | 4.99 |
| s44, 111 | 34.1 | 179.6 | 68.2 | −91.0 | −73.7 | 5.01 |
| y111 | −31.6 | −156.7 | 104.1 | −66.6 | −90.8 | 4.71 |
| y44, 111 | −32.9 | −157.0 | 164.5 | −67.5 | −89.8 | 4.73 |
| Literature[b]: | | | | | | |
| class 3 | 71(9) | −166(13) | 103(2) | −78(5) | −62(8) | 5.00 |
| class 6 | −55(3) | −121(11) | 101(3) | −83(4) | −53(7) | 4.18 |

[a]The first five columns of numbers are the dihedral angles for N—$C_\alpha$—$C_\beta$—S, $C_\alpha$—$C_\beta$—S—S', $C_\beta$—S—S'—$C_\beta'$, S—S'—$S_\beta'$—$C_\alpha'$, and S—$C_\beta'$—$C_\alpha'$—N', in the direction of $V_H44$ to $V_L105$ for the S1 site and in the direction of $V_L48$ to $V_H111$ for the S2 site.
[b]From Katz et al., infra. The quoted values are averages over 4 examples for class 3 and 8 examples for class 6, each with the standard deviation in parentheses.

10. Energies of the Disulfide Bonded Models

The stability of any of these mutants is difficult to estimate because of the lack of structural information of the corresponding unfolded forms. The various energy terms of the fully refined models are listed in Table 2. In considering these energy terms, one should bear in mind that the precise values are subject to the inherent uncertainties associated with the empirical potential energy functions and to the errors introduced by neglecting the solvent. These figures are meant to be used for qualitative considerations only.

Comparing first the energies of sites S1 and S2 of species B3 Fv and B3 yFv, it can be seen that the S1 site has a substantially lower energy than the S2 site before the mutation. This means that, if the mutated forms had the same energy, mutating the S1 site will be energetically more costly than mutating the S2 site. These energy values are, however, especially unreliable because the residues involved before the mutation are Arg, Ser, and Gln, which are all highly polar, and the energy value will be sensitively affected by the absence of the solvent.

On the other hand, the internal energy of the cysteine residue present at S1 after the mutation is about 6 kcal/mole lower than that present at S2, both in the singly and in the doubly disulfide bonded species. This is true whether the $V_H95$ is Ser or Tyr. Although this is a small energy difference, this calculation should be more reliable since it involves one covalently bonded moiety with no formal charge. Examination of the detailed composition of this energy difference indicates that most of at arises from the difference in the energy of the bond angle, which accounts for 3–4 kcal/mole, and from that of the torsion angle, which accounts for 1–2 kcal/mole. This indicates that the disulfide bond at S2 is slightly more strained than that at S1.

The interaction energy with the rest of the molecule rises by about 40 kcal/mole for site S1 and by about 30 kcal/mole for site S2, favoring S2. There is a much larger change in the energy of the rest of the molecule at sites other than S1 and S2, which implies that a conformational change occurs in this part of the molecule. However, a detailed examination of the structural changes and various energy components indicates that only a minor part of these differences can be traced to be a direct result of the introduction of the disulfide bond. The major part of the difference appears to be due to natural flexibility of the molecule at the exposed loops, coupled with the fact that the computed energy values are sensitive to small changes in the position of charged, flexible side chain atoms. In general, however, it appears that the energy of the molecule increases upon introduction of a disulfide bond and that it rises proportionately more when two disulfide bonds are formed. The magnitude of the rise per disulfide bond is comparable to that of the S1 site, i.e. the energy change upon converting an Arg and Ser to two Cys. It can also be noted that the $V_H$-$V_L$ interaction energy generally increases in magnitude upon the Tyr mutation at $V_H95$.

11. Geometries of the Disulfide Bonded Models

All disulfide bonds are found to be right-handed (Table 3). The cysteine reside formed at site S1 is approximately related to that formed at site S2 by the pseudo two-fold symmetry of the molecule. However, their detailed geometries (Table 3) indicate that they fall two types. All but two of the eight cysteine-residues are of one type (type A) while the remaining two, the one at S2 in species s111 and s44,111, are of a different type (type B). Katz et al., *J. Biol. Chem.* 261:15480–15485 (1986), incorporated by reference herein, surveyed the conformation of cysteine residues in known protein crystal structures and classified the right-handed forms into six different classes. The two types found in our models do not exactly fit into any of these classes. The dihedral angel values of two classes that fit the modeled geometry best are also included in Table 3. Class 6, with 8 examples, represents the most common geometry for the right-handed cysteine residues found in other protein structures. The internal dihedral angles of the disulfide bonds at side S1 are rather close to those in this class. On the other hand, the disulfide bonds at side S2 have internal dihedral angles that deviate much from their closest classes (class 6 for type A bonds in the y111 and y4,111 species and class 3 for the type B bonds in the s111 and s44,111 species).

The large deviation of Type B geometry from that of other disulfide bonds is probably related to the existence of the cavity near the S2 site in B3(Fv) at the bottom of which is $V_H95$ series residue. The new disulfide bond is at the side of this cavity and the $C_\beta$ atom of $V_L48$ residue is pulled in toward this cavity. The large deviation of the $C_\alpha$-$C_\beta$-S-S' and $C_{62}$-S-S'-$C_\beta$ dihedral angles of type B from those of others in class 3 is related to this distortion of the main-chain. The Tyr mutation at $V_H95$ fills this cavity with the Tyr side chain and appears to restore the main-chain distortion and to change the geometry of the cysteine residue from type B to type A. Even after the mutation, however, the geometry of the disulfide bond at S2 site deviates more from the class 6 geometry than that at S1 site.

The main-chain dihedral angle values (Table 4) indicate that mutation at S1 has no effect on the geometry of the main-chain at S2 and vice versa. Large angle changes are restricted to the mutated residue in the heavy chain. The sole exception is the 30° change in the ψ angle of $V_H110$ for the S11 and s44,111 species, a feature probably related to the existence of the cavity near S2 in these species. The Tyr mutation at $V_H95$ changes this and other main-chain dihedral angles at S2 (Φand ψ of $V_L48$ and ψ of $V_H100$ and $V_H111$).

12. Modeling Conclusion.

It is well known that each of the heavy and light chains of the Fv fragment forms a nine-stranded beta-barrel and that the interface between the heavy and light chains that forms at the center of the molecule is also barrel-shaped (Richardson, *Adv. Prot. Chem.* 34:167–339 (1981)). One side of this central barrel is made of four strands from the heavy chain while the other side is made of four strands from the light chain. These two sides join each other around the barrel at two side, which are related by the approximate two-fold symmetry that runs along the axis of the barrel (Davies et al., *Ann. Rev. Biochem.* 44:639–667 (1975)). At each site, a stretch of the β4 strand of one chain ($V_H44$-47 or $V_L48$-51 for B3 Fv) is next to, and runs antiparallel to, a stretch of the β9 strand of the other chain ($V_L105$-101 or $V_H111$-107 for B3 Fv). In the modeled structure of B3 Fv, and probably in the Fv of all immunoglobulins, the closest inter-chain contacts between the mainchain atoms in the FR region occur either within these stretches or at the immediate fringes of these stretches (Table 1). Since the $C_\alpha$—$C_\alpha$ distance of a cysteine residue in known protein structure ranges from 4.2 to 6.6 Å (Katz et al., *J. Biol. Chem.* 261:15480–15485 (1986)), it is improbably that an inter-chain disulfide bond can be formed in the FR region outside of these sites, without introducing large, damaging distortions to the molecule.

The two possible disulfide bonding sites studied in this report at the shortest contact points in each of these sites (Table 1). The disulfide bonds at $V_H44$-$V_L106$, $V_H112$-$V_L48$, and $V_H111$-$V_L47$ are also good sites. Other pairs with short $C_\alpha$—$C_\alpha$ distances are less preferable since they are closer to the CDR loops in the three-dimensional structure and therefore more likely to disturb the antigen binding function of the molecule.

However, both of the sites they used for McPC603 $V_H108$-$V_L5$ and $V_H106$-$V_L56$ involved residues in the CDR region and obviously were not the two sites that we identified. These sites correspond to $V_H105$-$V_L54$ and $V_H103$-$V_L5$ of B3 and are at the extreme CDR end of the β4/β9 strands, at the opposite end of which lies the S2 sites of $V_H111$-$V_L48$. This difference results at least in part from the different strategy used to search for the potential disulfide bond sites: they searched for interchain residue pairs, neither of which was Pro, and all of whose main-chain atoms were arranged in a geometry similar (within 2 Å in rms) to that of a cysteine residue in a list of all such residues in known protein structures. They avoided the residues directly involved in the hapten binding, but otherwise allowed them to be in the CDR region. In contrast, we searched for sites strictly in the FR region only, while relaxing on the constraints on geometry by requiring only that their $C_\alpha$ to $C_\alpha$ distance be short. We reasoned that a distortion at the site of mutation was inevitable and that an insistence on a similarity of the whole main-chain before the disulfide bond formation was probably too restrictive.

The calculated main-chain dihedral angle values (Table 4) indicate that disulfide bonds can be formed at these sites without a large change in the internal geometry of the main-chain. The calculated main-chain dihedral angle values (Table 4) indicate that disulfide bonds can be formed without a large change in the internal geometry of the main-chain. In particular, the changes in the main-chain dihedral angles of the flanking Gly residues, which we initially thought would help absorb some of the distortions, are small. The internal geometries of the cysteine residues formed (Table 3) appear to be close to the geometries of other cysteine residues in known protein structures, at least at one of the two sites. The calculated energy values must be used with caution because of the inherent uncertainties associated with the empirical potential function used, because the solvent was not included in the calculation, and because the calculation is possible only for the folded form whereas what is needed is the difference between the folded and unfolded forms. The calculations nevertheless indicate (Table 2) that the energetic cost for introducing a disulfide bond at the two sites will be basically that of converting the character of two-residue's worth of the protein surface from charged to non-polar. All of these indicated to us that introduction of a disulfide bond at one of these two sites would be possible.

The main-chain geometries and the internal geometries of the cysteine residue, as well as the $V_H$-$V_L$ interaction energies, indicate that the Ser to Tyr mutation at $V_H95$ is likely to be beneficial. The energetic considerations indicate that the species y44 and y111 would be roughly equally suitable and preferable over the double disulfide bonded species. Finally, the comparison of the internal geometry of the cysteine residue with that of others in known protein structures gives a slight edge for the y44 species over the y111.

TABLE 4

The main chain dihedral angles, φ (first angle) and ψ, in degrees, of indicated residues in various species of B3 Fv.

| | $V_H44$ (R, C) | | $V_L104$ (G) | | $V_L105$ (S,C) | | $V_L106$ (G) | |
|---|---|---|---|---|---|---|---|---|
| B3 Fv | −91.5 | −164.5 | −69.6 | 172.7 | −80.5 | −10.6 | 94.0 | 119.8 |
| B3 yFv | −91.5 | −165.2 | −69.2 | 172.4 | −79.4 | −11.6 | 95.0 | 119.1 |
| s111 | −89.1 | −168.0 | −70.5 | 171.8 | −79.2 | −13.3 | 94.3 | 121.3 |
| y111 | −93.9 | −165.6 | −69.8 | 172.4 | −79.6 | −11.3 | 94.4 | 120.0 |
| s44 | −134.4 | −173.1 | −85.8 | 164.8 | −87.9 | −1.0 | 104.5 | 137.2 |
| s44, 111 | −109.8 | −169.8 | −86.5 | 163.5 | −88.0 | 1.7 | 102.1 | 141.6 |
| y44 | −128.2 | −173.2 | −85.7 | 167.2 | −89.0 | −2.6 | 104.8 | 135.1 |
| y44, 111 | −141.0 | −175.1 | −86.6 | 162.1 | −85.0 | −3.6 | 106.8 | 137.9 |

| | $V_L48$ (S, C) | | $V_H110$ (G) | | $V_H111$ (O, C) | | $V_H112$ (G) | |
|---|---|---|---|---|---|---|---|---|
| B3 Fv | −84.5 | 154.7 | −86.4 | −144.9 | −106.4 | −43.8 | 111.2 | 141.6 |
| B3 | −85.8 | 146.7 | −85.5 | −141.6 | −108.8 | −45.1 | 115.6 | 142.1 |

TABLE 4-continued

The main chain dihedral angles, φ (first angle) and ψ, in degrees, of indicated residues in various species of B3 Fv.

| yFv | | | | | | | | |
|---|---|---|---|---|---|---|---|---|
| s44 | −85.0 | 153.8 | −87.0 | −145.1 | −107.0 | −44.4 | 111.7 | 142.1 |
| y44 | −85.7 | 145.5 | −86.4 | −144.3 | −117.2 | −42.5 | 118.2 | 138.0 |
| s111 | −88.6 | 151.4 | −88.7 | −172.7 | −130.6 | −5.4 | 116.2 | 138.6 |
| s44, 111 | −89.9 | 151.4 | −88.7 | −171.6 | −131.0 | −5.6 | 115.7 | 139.0 |
| y111 | −79.0 | 131.7 | −86.8 | −149.1 | −135.3 | −17.0 | 114.1 | 136.0 |
| y44, 111 | −80.0 | 132.9 | −87.1 | −151.1 | −133.9 | −16.4 | 113.0 | 135.9 |

The fact that the disulfide bond sites found here are in the highly conserved framework region is significant. The Cys mutant at these sites is expected to work because the structure of the framework region is relatively similar from protein to protein. As a partial test of this expectation, we have computed the $C_\alpha$—$C_\alpha$ distances at these sites using the crystal structures for all known immunoglobulin Fv regions. These data (Table 5) indicate that, while there are variations, the $C_\alpha$—$C_\alpha$ distances are indeed suitably short for formation of a disulfide bond at at least one of the sites in all the proteins including some from the human source. These sites can be found for any immunoglobulin simply from the sequence alignment without the need for computer modeling or structural information.

TABLE 5

The $C_\alpha$—$C_\alpha$ distances (in Angstroms) between residue pairs in immunoglobulins[a] at positions homologous to those of $V_H44$–$V_L105$ and $V_H111$–$V_L48$ in B3.

| B3 model | $V_H44R$–$V_L105S$ | 5.6 | $V_H110Q$–$V_L48S$ | 5.6 |
|---|---|---|---|---|
| 1MCP | $V_H44R$–$V_L106A$ | 5.6 | $V_H114A$–$V_L49P$ | 5.7 |
| 2FB4 | $V_H44G$–$V_L101T$ | 6.0 | $V_H110Q$–$V_L42A$ | 5.4 |
| 2FBJ | $V_H44G$–$V_L99A$ | 5.8 | $V_H110Q$–$V_L42S$ | 5.8 |
| 2IG2 | $V_H44G$–$V_L101T$ | 5.9 | $V_H111Q$–$V_L42A$ | 4.9 |
| 3FAB | $V_H44G$–$V_L101G$ | 5.3 | $V_H109Q$–$V_L42A$ | 6.0 |
| 1FAI | $V_H44G$–$V_L100G$ | 4.4 | $V_H116Q$–$V_L43T$ | 6.4 |
| 2F19 | $V_H44G$–$V_L100G$ | 4.1 | $V_H116Q$–$V_L43T$ | 5.6 |
| 1FDL | $V_H44G$–$V_L100G$ | 5.4 | $V_H108Q$–$V_L43S$ | 5.6 |
| 1IGF | $V_H44R$–$V_L100G$ | 5.9 | $V_H115Q$–$V_L43S$ | 6.3 |
| 2HFL | $V_H44G$–$V_L98G$ | 4.6 | $V_H108Q$–$V_L42S$ | 5.8 |
| 3HFM | $V_H44R$–$V_L100G$ | 6.4 | $V_H105Q$–$V_L43S$ | 6.0 |
| 4FAB | $V_H44G$–$V_L105G$ | 6.8 | $V_H110Q$–$V_L48S$ | 5.3 |
| 6FAB | $V_H44G$–$V_L100G$ | 5.2 | $V_H113Q$–$V_L43T$ | 6.2 |

[a]The immunoglobulins are identified by the Bookhaven Data Bank file names (Abola et al., supra). All are from the mouse except three (2FB4, 2IG2, and 3FAB) which are from the human.

II. Production of a B3 (dsFv) immunotoxin.

B3 (dsFv)-PE38KDEL is a recombinant immunotoxin composed of the Fv region of MAb B3 connected to a truncated form of Pseudomonas exotoxin (PE38KDEL), in which the $V_H$-$V_L$ are held together and stabilized by a disulfide bond.

A. Construction of plasmids for expression of B3(dsFv)-immunotoxins.

The parent plasmid for the generation of plasmids for expression of ds(Fv)-immunotoxins, in which $V_H$Arg44 and $V_L$ser105 are replaced by cysteines, encodes the single-chain immunotoxin B3(Fv)-PE38KDEL(Tyr H95). In this molecule the $V_H$ and $V_L$ domain of MAb B3 are held together by a $(Gly_4Ser)_3$ (SEQ ID NO:23) peptide linker (B3scFv) and then fused to the PE38KDEL gene encoding the translocation and ADP-ribosylation elements of Pseudomonas exotoxin (PE) (Brinkmann et al., Proc. Natl.

Acad. Sci. USA 89:5867–5871 (1991) (Brinkmann I); Hwang et al., Cell 48:129–136 (1987), both of which are incorporated by reference herein). B3(Fv)-PE38KDEL(Tyr H95) is identical to B3(Fv)-PE38KDEL (Brinkmann I, supra) except for a change of serine 95 of B3($V_H$) (position $V_H$91 according to Kabat et al.), to tyrosine. This tyrosine residue is conserved in the framework of most murine $V_H$ domains and fills a cavity in the $V_H$-$V_L$ interface, probably contributing to $V_H$-$V_L$ domain interactions. We have compared the properties of B3(Fv)-PE38KDEL and B3(Fv)-PE38KDEL(Tyr H95), including ability to be renatured, behavior during purification, and cytotoxic activity towards carcinoma cell lines, and found them to be indistinguishable.

The plasmids for expression of the components of ds(Fv)-immunotoxins, B3($V_N$Cys 44) and B3($V_L$Cys105)-PE38KDEL were made by site-directed mutagenesis using uridine containing single-stranded DNA derived from the F+ origin in pULI28 as template to mutate Arg44 in B3($V_H$) and Ser105 in B3($V_L$) to cysteines (Kunkel, Proc. Natl. Acad. Sci. USA 82:488–492 (1985)), see below for sequences of the mutagenic oligonucleotides. The final plasmids pYR38-2 for expression of B3($V_H$Cys44) and pULI39 for B3($V_L$Cys105)-PE38KDEL were made by subcloning from the mutagenized plasmids. Details of the cloning strategy are shown in FIG. 2.

Plasmid constructions:

Uracil-containing single stranded DNA from the F+ origin present in our expression plasmids was obtained by cotransfection with M13 helper phase and was used as template for site directed mutagenesis as previously described (Kunkel, T. A., Proc. Natl. Acad. Sci. USA 82:488–492 (1985)). The complete nucleotide sequence of B3(Fv) has been described before (Brinkmann I, supra). The mutagenic oligonucleotides were 5'-TATGCGACCCA CTCGAGACACTTCTCTGGAGTCT-3' (SEQ ID NO:5) to change Arg44 of B3($V_H$) to Cys, 5'-TTTCCAGCTTTGTCCCACAGCCGAACGTGAATGG-3' (SEQ ID NO:6) to replace Ser105 of B3($V_L$) with Cys, and 5'-CCGCCACCACCGGATCCGC GAATTCATTAGGAGACAGTGACCAGAGTC-3' (SEQ ID NO:7) to introduce stop codons followed by an EcoRI site at the 3'-end of the B3($V_H$) gene. Restriction sites (XhoI and EcoRI) introduced into these oligonucleotides to facilitate identification of mutated clones or subcloning are underlined. The oligonucleotides 5'TCGGTTGGAAACTTTG-CAGATCAGGAGCTTTGGAGAC3' (SEQ ID NO:8), 5'TCGGTTGGAAACGCAGTAGATCA-GAAGCTTTGGAGAC3' (SEQ ID NO:9), 5'AFTAAG-CAAACCAGGCGCACCAGGCCAGTCCTCT-TGCGCAGTAATATATGGC3' (SEQ ID NO:10), and 5'AFTAAGCAAAACAGGCTCCCCAGGC-CAGTCCTCTTGCGCAGTAATATATGGC3' (SEQ ID NO:11) were used to introduce cysteines at $V_L$54, $V_L$55, $V_H$103 and $V_H$105 of B3(Fv), which correspond to the positions $V_L$55, $V_L$56, $V_H$106 and $V_H$108 of the described disulfide-stabilized McPC603 Fv (Glockshuber et al., supra; see Table 7). All mutated clones were confirmed to be correct by DNA sequencing. The B3($V_L$Cys105) mutation was subcloned into a B3($V_L$)-PE38KDEL immunotoxin coding vector by standard techniques according to Sambrook et al., Molecular Cloning: A Laboratory Manual (2nd ed.), Vols. 1–3, Cold Spring Harbor Laboratory (1989), incorporated by reference herein (see also FIG. 2).

B. Expression in inclusion bodies, refolding and purification.

B3(Fv)-PE38KDEL, B3(Fv)Cys H44L105-PE38KDEL, B3($V_L$Cys105)-PE38KDEL and B3($V_H$Cys44) were produced in separate E. coli BL21 λDE3 cultures containing pULI9, pULI37, pULI39 or pYR38-2 respectively, essentially as described (Brinkmann I, supra).

To produce recombinant B3(dsFv)-immunotoxins, separate E. coli BL21 (λDE3) cultures containing either the B3($V_H$Cys44) encoding plasmid pYR38-2 or the B3($V_L$Cys105)-PE38KDEL encoding plasmid pULI39 were induced with IPTG, upon which the recombinant proteins accumulated to 20–30% of the total protein in intracellular inclusion bodies (IBs). Active immunotoxins were obtained after the IBs were isolated separately solubilized, reduced and refolded in renaturation buffer containing redox-shuffling and aggregation preventing additives. The refolding for dsFv was performed as previously described for the preparation of single-chain immunotoxins (Buchner et al., Anal. Biochem. 205:263–270 (1992), incorporated by reference herein) with two modifications: (i) Instead of adding only one solubilized and reduced protein (e.g. B3(Fv) PE38KDEL) to the refolding solution, we prepared IBs containing $V_H$Cys44 or $V_L$Cys105-toxin separately and mixed them in a 2($V_H$):1($V_L$-toxin) molar ratio to a final total protein concentration of 100 µg/ml in the refolding buffer. We found that a 2–5 fold excess of $V_H$ over the $V_L$-toxin gave the best yield of renatured immunotoxin. Equal molar addition of $V_H$ and $V_L$-toxin into the renaturation solution or a >5 fold excess of $V_H$ resulted in a reduction of the yield of active monomeric immunotoxin; with too much $V_H$ we observed increased aggregation. (ii) A "final oxidation" step in which excess oxidized glutathione was added to the refolding solution after the redox-shuffling was completed. This oxidation increased the yield of properly folded functional protein by at least five-fold, probably because the disulfide bond connecting $V_H$ and $V_L$ is exposed on the surface of the Fv and is accessible to the slight reducing conditions in the refolding buffer and would remain reduced without "final oxidation."

To recover active immunotoxins after refolding, we adapted the purification scheme established for scFv-immunotoxins (Brinkmann I, supra; Brinkmann et al., J. Immunol. 150:2774–2782 (1993) (Brinkmann II), incorporated by reference herein; Buchner et al., supra), which is ion-exchange chromatography (Q-sepharose and MonoQ columns) followed by size exclusion chromatography. Properly folded (dsFv)-immunotoxins have not only to be separated from aggregates, which separate easily, but also from "single-domain" $V_L$-toxins which have a chromatographic behavior close to (dsFv)-immunotoxins (Brinkmann II, supra). After refolding of B3(dsFv)-PE38KDEL, the MonoQ "monomer peak" contains two proteins; the dsFv-immunotoxin elutes slightly earlier than the $V_L$-toxin. We purified B3(dsFv)-PE38KDEL to near homogeneity by consecutive cycles of chromatography, pooling early fractions, rechromatographing peak fractions and discarding late fractions. Despite significant losses of active dsFv-immunotoxin (discarded "late" fractions still contain dsFv-protein), this procedure is efficient enough to obtain >8 mg pure dsFv-immunotoxin from 1 liter each of bacterial $V_H$ and $V_L$-toxin cultures and we expect to greatly increase this yield by modifying our purification conditions.

III. Specific toxicity of B3(dsFv)-PE38KDEL towards B3-antigen expressing carcinoma cell lines.

The activity of different immunotoxins ($IC_{50}$ in ng/ml) towards carcinoma cell lines was determined as described in Tables 6 and 7. B3(scdsFv)-PE38KDEL molecules are single-chain immunotoxins which in addition to the $(Gly_4Ser)_3$ linker (SEQ ID NO:23) have cysteines introduced in $V_H$ and $V_L$ to form an interchain disulfide. $V_H$44-

$V_L 105$ corresponds to B3(dsFv)-PE38KDEL, except that in B3(dsFv) the linker peptide is deleted. $V_H 105$-$V_L 54$ and $V_H 103$-$V_L 55$ are the positions where cysteine residues were introduced in the previously described "custom-made" $V_H 108$-$V_L 55$ and $V_H 106$-$V_L 56$ disulfide bonded McPC603 (Fv) (Glockshuber et al., supra).

TABLE 6

Cytotoxicity of recombinant B3-immunotoxins towards different cell lines

| Cell Line | Cancer Type | B3-Ag | Cytotoxicity in ng/ml ($IC_{50}$) | |
|---|---|---|---|---|
| | | | B3(FV)-PE38KDEL | B3(dsFv)-PE38KDEL |
| MCF7 | Breast | +++ | 0.25 | 0.25 |
| A431 | Epidermoid | +++ | 0.3 | 0.35 |
| LNCaP | Prostate | + | 9 | 8.5 |
| HTB103 | Gastric | + | 3.5 | 3.5 |
| HUT-102 | Leukemia | − | >1000 | >1000 |

*Estimated by immunofluorescence using MAb B3.

Cytotoxicity assays were performed by measuring incorporation of $^3$H-leucine into cell protein as previously described (Brinkmann et al., *Proc. Natl. Acad. Sci. USA* 88:8161–8620 (1991) (Brinkmann I), incorporated by reference herein) $IC_{50}$ is concentration of immunotoxin that causes a 50% inhibition of protein synthesis following a 16 hour incubation with immunotoxin.

Figure 3A:
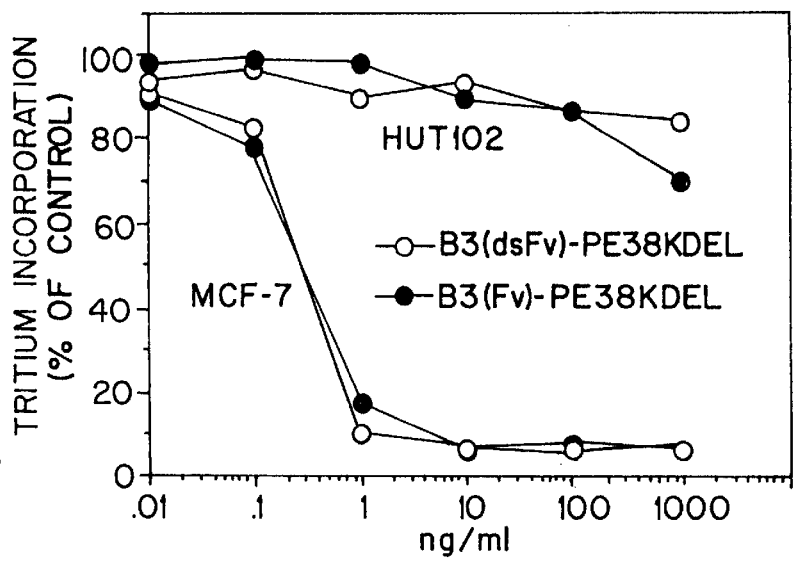
FIG. 3: Specific cytotoxicity of B3(dsFv)-PE38KDEL and B3(Fv)-PE38KDEL towards different carcinoma cell lines. (a) Comparison of cytotoxicity of B3(Fv)-PE38KDEL and B3(dsFv)-PE38KDEL towards B3-antigen expression A431 cell and B3-negative HUT-1002 cells; (b) Cytotoxicity of B3-dsFv)-PE38KDEL towards various cell lines; (c) Competition of cytotoxicity towards A431 cells by addition of excess MAb B3. Note that addition of equal amounts of isotype-matched control, MAb HB21, which binds to A431 cells but to a different antigen (transferring receptor) does not compete.
Figure 3B:
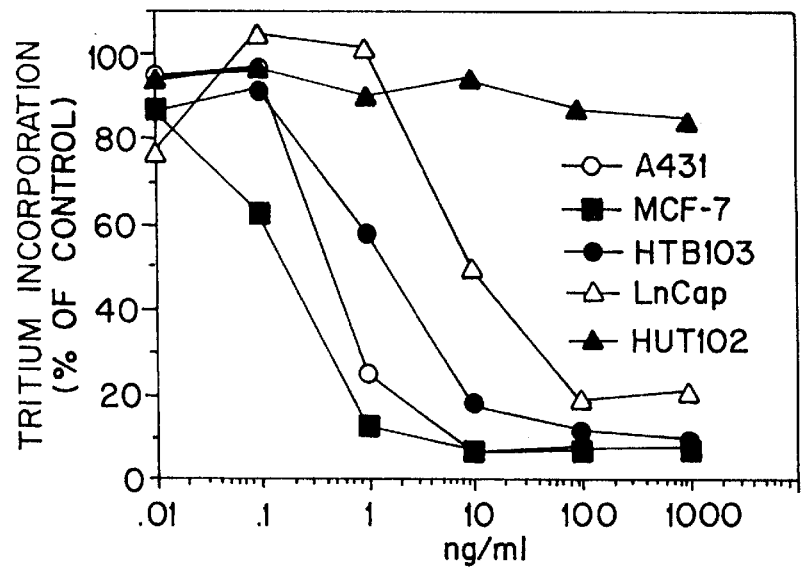
Figure 3C:
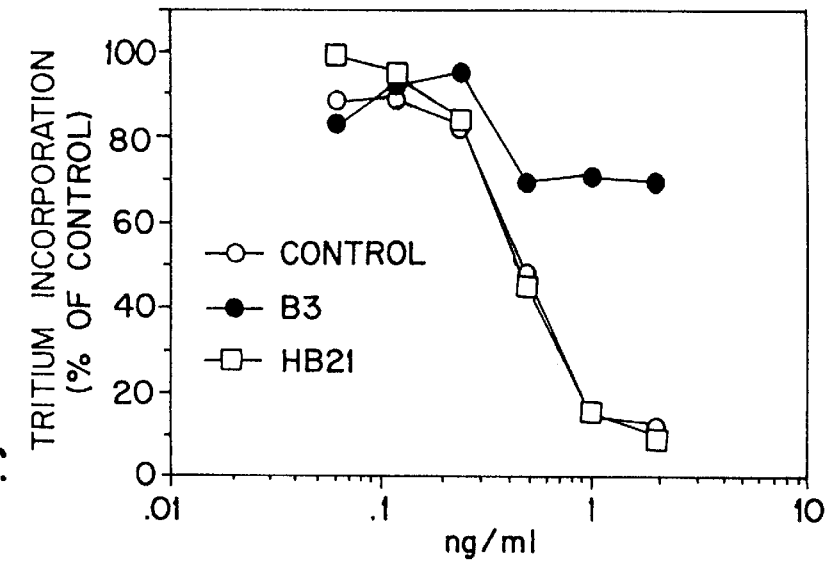

A comparison of Fv-mediated specific cytotoxicity of a single-chain immunotoxin B3(Fv)-PE38KDEL and the corresponding disulfide-stabilized B3(dsFv)-PE38KDEL shows that both proteins recognize the same spectrum of cells and are equally active (FIG. 3, Tables 6 and 7). B3(dsFv)-PE38KDEL like B3(Fv)-PE38KDEL only is cytotoxic to B3-antigen expressing cells and has no effect towards cells which do not bind MAb B3 (e.g., HUT102). The addition of excess MAb B3, but not an excess of HB21, an antibody to the human transferrin receptor, can compete with this cytotoxicity, confirming that the activity of B3(dsFv)-PE38KDEL is due to specific binding to the B3-antigen (FIG. 3C). In this competition experiment, excess MAb B3 or HB21 (to a final concentration of 1 mg/ml) was added 15 min before addition of toxin. A high concentration of MAb B3 is necessary for competition because of the large amount of B3-antigen present on carcinoma cells (Brinkmann I, supra; Brinkmann II, supra; Pai et al., *Proc. Natl. Acad. Sci. USA* 88:3358–3362 (1991)). The finding that the specificity and activity of scFv- and dsFv-immunotoxins are indistinguishable indicates that the binding region is conserved equally well in the disulfide-stabilized B3(Fv) and in the linker stabilized molecule.

TABLE 7

Placement of the disulfide bond connecting $V_H$ and $V_L$ at different positions of B3 (Fv) PE38KDEL fusion protein

| Cell Line | B3(Fv) | B3(dsFv) | B3(scdsFv) H44–L105 | B3(scdsFv) H105–L55 | B3(scdsFv) H103–L56 |
|---|---|---|---|---|---|
| A431 | 0.3 | 0.3 | 0.4 | 80 | 250 |
| MCF7 | 0.25 | 0.25 | 0.3 | 90 | 200 |

IV. Stability of B3(Fv)- and B3(dsFv)-PE38KDEL in human serum.

Because dsFv- and scFv-immunotoxins have equal activity towards cultured carcinoma cells, B3(dsFv)-PE38KDEL should also be useful for cancer treatment like its scFv counterpart, B3(Fv)-PE38KDEL (Brinkmann I, supra). One factor that contributes to the therapeutic usefulness of immunotoxins is their stability. The stability of Fv-immunotoxins was determined by incubating them at a concentration of 10 μg/ml at 37° C. in human serum. Active immunotoxin remaining after different lengths of incubation was determined by cytotoxicity assays on A431 cells. Table 8 shows a comparison of the stability of scFv- and dsFv-immunotoxins in human serum. The scFv-toxin B3(Fv)-PE38KDEL is stable for one to two hours and then begins to lose activity. In marked contrast, the dsFv-toxin B3(dsFv)-PE38KDEL retains full cytotoxic activity for more than 24 hours.

TABLE 8

Stability of B3 (Fv)-PE38KDEL and B3 (dsFv)-PE38KDEL in human serum

| Sample | % activity left Hours | | | | | | | |
|---|---|---|---|---|---|---|---|---|
| | 0 | 0.5 | 1 | 2 | 4 | 8 | 12 | 24 |
| ScFv in Serum 1 | 100 | 100 | 87 | 50 | 31 | 14 | 14 | 1 |
| scFv in serum 2 | 100 | 88 | 58 | 35 | 20 | 6 | 4 | 1 |
| dsFv in serum 1 | 100 | 100 | 100 | 100 | 100 | 100 | 100 | 100 |
| dsFv in serum 2 | 100 | 100 | 100 | 100 | 100 | 100 | 100 | 100 |

Each type of immunotoxin was incubated at 10 μg with human serum at 37° C. for the times shown and then assayed for cytotoxic activity on A431 cells.

V. Immunotoxin e23(Fvds)-PE38KDEL.

MAb e23 is an antibody directed against the erbB2 antigen which is present on many human carcinoma. e23(Fv)-PE40 is a single chain immunotoxin composed from the single-chain Fv of e23 which $V_L$ is connected by peptide linker to $V_H$ which in turn is fused to a truncated form of Pseudomonas exotoxin (PE40). e23(Fv)PE40 has been shown to be of potential use in cancer therapy (Batra et al., *Proc. Natl. Acad. Sci. USA* 89:5867–4871 (1992)). e23(Fv)-PE38KDEL is a single chain derivative of e23(Fv)-PE40 in which the toxin part of the immunotoxin is PE38KDEL instead of PE40 which results in improved activity.

A. Position of the disulfide.

The Fv region of e23 can be stabilized by a disulfide bond in the same manner as described for B3(Fv) above. We made the immunotoxin e23(dsFv)-PE38KDEL which corresponds in its composition to e23 (scFv)-PE38KDEL, except that it has the peptide linker between $V_L$ and $V_H$ omitted and replaced by a disulfide bond. The positions that we used for introduction of the disulfide are corresponding to position $V_H 44$-$V_L 100$ according to Kabat and Wu, and position $V_H$ Asn43 and $V_L$ Gly99 in the actual e23 sequence, see FIG. 4.

B. Plasmid constructions.

The replacement of framework residues by cysteines, deletion of the linker peptide and construction of plasmids for separate expression of the components of the e23(dsFv) immunotoxin was done by standard mutagenesis and cloning techniques as described in the example above. Mutagenic oligonucleotides hat were used for replacement of $V_H$ Asn43 and $V_L$ Gly99 with cysteines were 5'-AGTCCAATCCACTCGAGGCACTTTCCATGGCTCT GC-3' (SEQ ID NO:12) ($V_H$) and 5'-TATTTCCAGCTTGGACCCACATCCGAACGTGGGT GG-3'

Figure 5:
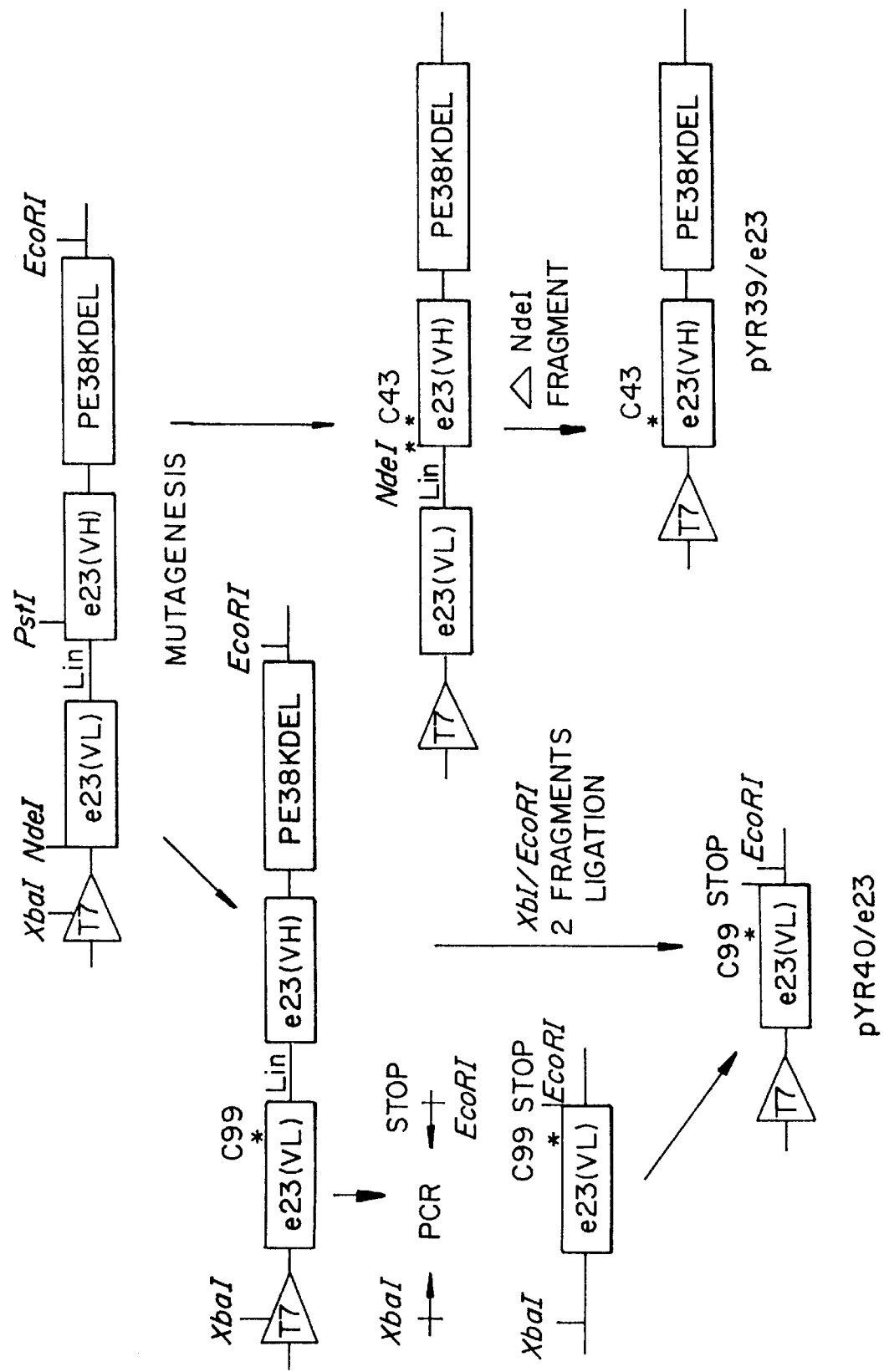
FIG. 5: Plasmid construction for expression of e23(dsFv)-PE38KDEL.

(SEQ ID NO:13) ($V_L$), stop codon at the end of the $V_L$ was introduced by the primer 5'-AGAAGATTTACCAGAACCAGGAATTCATTATTTTATTTGCAGCTTGGACC-3' (SEQ ID NO:14). Details of the plasmid constructions are described in FIG. 5. Note, that in contrast to B3(Fv)-immunotoxins, the toxin portion of e23(Fv)-immunotoxins, e23(scFv) and e23(dsFv)-PAE38KDEL is fused to the $V_H$ and not to the $V_L$ domain of the Fv.

C. Production of e23(dsFv)-PE38KDEL.

The components of e23(dsFv)-PE38KDEL, which are e23($V_L$Cys99) and e23($V_H$Cys43)-PE38KDEL were expressed separately in *E. coli* in inclusion bodies which were isolated and refolded as described above. Active proteins were isolated by ion exchange and size exclusion chromatography essentially described above. We found, however, that in contrast to purification of B3(dsFv)-immunotoxins, the preparation did not contain as much contaminating "single domain" immunotoxins. This is because in the B3(dsFv)-immunotoxin example, the toxin is fused to $V_L$, while in the e23dsFv immunotoxin the toxin is fused to $V_H$. It has been described, that single domain $V_L$-toxins are much more soluble than $V_H$-toxins, which strongly tend to aggregate. Because of that, in the B3(dsFv) example, soluble $V_L$-toxin molecules can severely contaminate the dsFv-immunotoxin preparation, while in the e23 (dsFv)-example the contaminating $V_H$-toxins aggregate and precipitate, and thus can be easily removed from the dsFv-immunotoxin.

D. Comparison of scFv and dsFv of e23.

As described above, specific cytotoxicity of Fv-immunotoxins can be used to assess the specific binding of the Fv portion of the immunotoxin. The comparison of the specific cytotoxicity of scFv and dsFv-immunotoxins derived from MAb e23 on cells that have erbB2 on their surface are listed in Table 9 (See Table 6 and related discussions for protocol details). The dsFv-immunotoxin of e23 is at least as active and even might be slightly more active than the scFv counterpart. Thus, the specific binding of the dsFv of e23 to erbB2 is the same or superior to e23(scFv).

TABLE 9

| Cell-Line | Cancer | e23 (scFv) PE38KDEL | e23 (dsFv) PE38KDEL |
|---|---|---|---|
| N87 | gastric | 0.2 ng/ml | 0.06 ng/ml |
| HTB20 | breast | 0.075 ng/ml | 0.06 ng/ml |

What is claimed is:

1. A nucleic acid that encodes a light chain variable region ($V_L$) of an antibody wherein the $V_L$ contains a cysteine at position 42, 43, 44, 45, 46, 98, 99, 100, or 101, such positions being determined in accordance with the numbering scheme published by Kabat and Wu.

2. A nucleic acid of claim 1, which encodes a cysteine at position 100 of the $V_L$.

3. A nucleic acid of claim 1, which encodes a cysteine at position 43 of the $V_L$.

4. A nucleic acid that encodes a heavy chain variable region ($V_H$) of an antibody wherein the $V_H$ contains a cysteine at position 43, 44, 45, 46, 47, 103, 104, 105 or 106, such positions being determined in accordance with the numbering scheme published by Kabat and Wu.

5. A nucleic acid of claim 4, which encodes a cysteine at position 4 of the $V_H$.

6. A nucleic acid of claim 4, which encodes a cysteine at position 105 of the $V_H$.

7. The nucleic acid of claim 1 which further includes a nucleic acid that encodes a toxin or pharmaceutical agent.

8. The nucleic acid sequence of claim 7, wherein the toxin or pharmaceutical agent is connected to the antibody by a peptide linker.

* * * * *